(12) United States Patent
Miller et al.

(10) Patent No.: US 11,006,912 B2
(45) Date of Patent: May 18, 2021

(54) METHODS, SYSTEMS, AND COMPUTER-READABLE STORAGE MEDIA FOR ENHANCED PHASE-CONTRAST X-RAY IMAGING

(71) Applicant: BATTELLE MEMORIAL INSTITUTE, Richland, WA (US)

(72) Inventors: Erin A. Miller, Richland, WA (US); Richard E. Jacob, Kennewick, WA (US); Nikhil S. Deshmukh, Everett, WA (US); Cynthia L. Warner, Richland, WA (US); Richard S. Wittman, Richland, WA (US); Luke W. Campbell, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 16/363,989

(22) Filed: Mar. 25, 2019

(65) Prior Publication Data
US 2020/0305812 A1    Oct. 1, 2020

(51) Int. Cl.
*G01N 23/041*    (2018.01)
*A61B 6/00*    (2006.01)

(52) U.S. Cl.
CPC .......... *A61B 6/4291* (2013.01); *A61B 6/405* (2013.01); *A61B 6/4035* (2013.01); *A61B 6/466* (2013.01); *A61B 6/484* (2013.01)

(58) Field of Classification Search
CPC .......... A61B 6/00; A61B 6/484; A61B 6/483; A61B 6/4241; A61B 6/4291; A61B 6/405; A61B 6/4035; G21K 2207/005; G01N 23/04; G01N 23/041; G01N 2223/303; G01N 2223/3035
USPC .................................. 378/36, 62, 87, 207
See application file for complete search history.

(56) References Cited

U.S. PATENT DOCUMENTS

| | | | |
|---|---|---|---|
| 5,812,629 A * | 9/1998 | Clauser | A61B 6/032 378/37 |
| 9,357,975 B2 * | 6/2016 | Baturin | G01N 23/041 |
| 2012/0163554 A1 * | 6/2012 | Tada | A61B 6/4291 378/154 |
| 2012/0201349 A1 * | 8/2012 | Kaneko | A61B 6/4291 378/62 |

* cited by examiner

*Primary Examiner* — Jurie Yun
(74) *Attorney, Agent, or Firm* — Klarquist Sparkman, LLP

(57) ABSTRACT

Systems and methods that directly image attenuation-based object grid, use a source grid to improve imaging of the object grid using a high-energy polychromatic source, and use a detector grid having gratings oriented substantially orthogonally to that of the object grid, can address artifacts and beam hardening effects that limit the quality and discriminatory power of high-energy x-ray imaging that includes phase contrast.

21 Claims, 18 Drawing Sheets

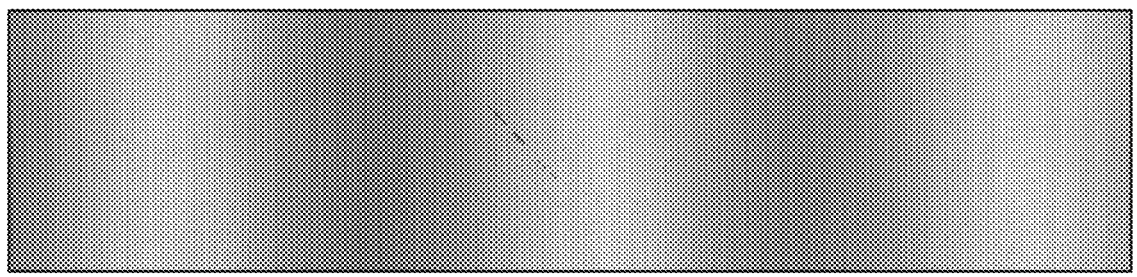
FIG. 18A
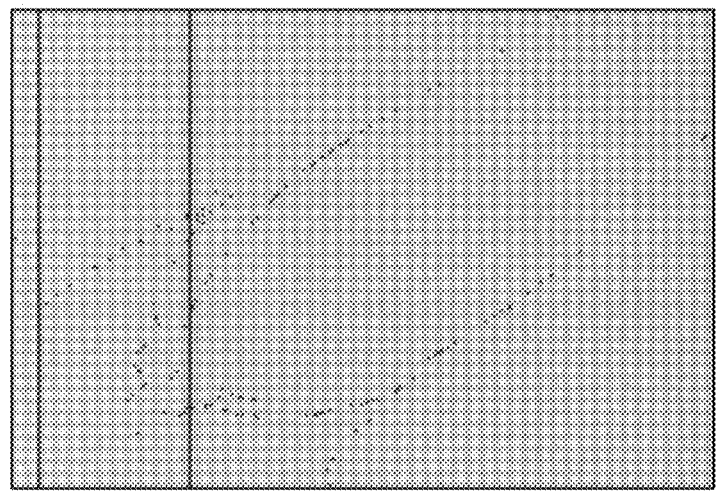
FIG. 18B
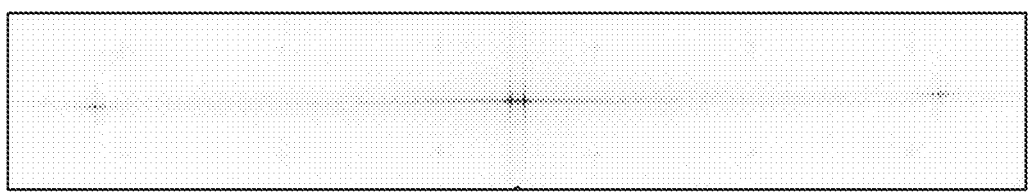
FIG. 19A
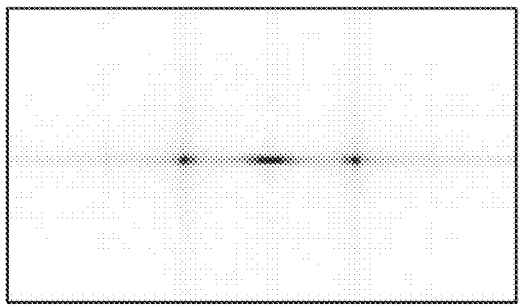 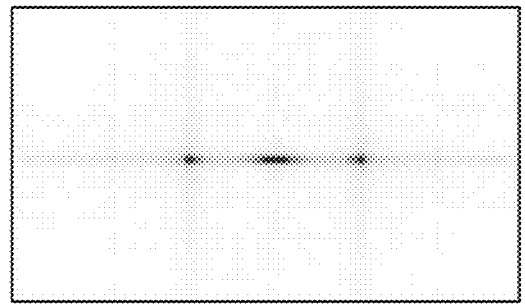
FIG. 19B　　　FIG. 19C

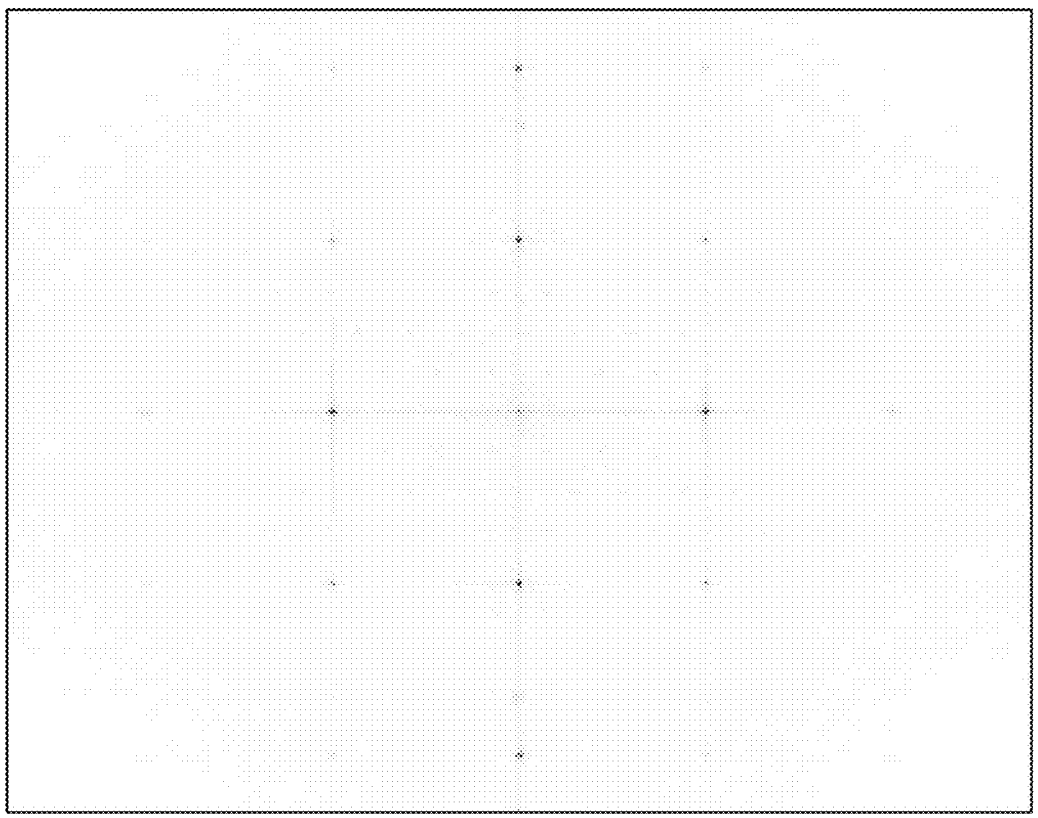
FIG. 20
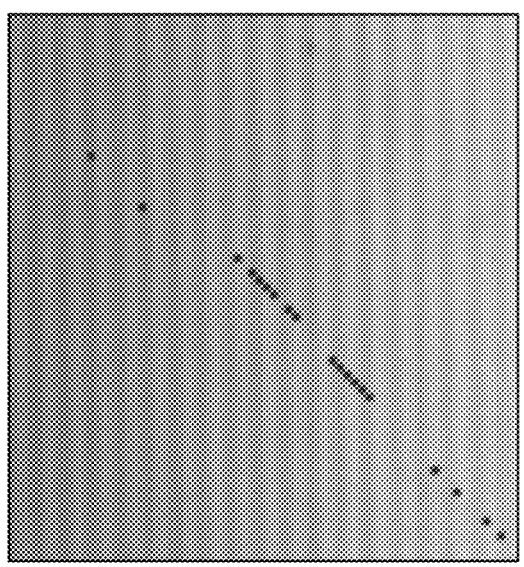 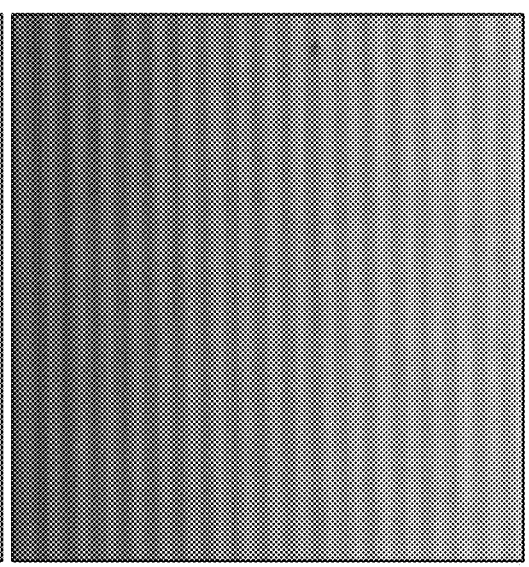
FIG. 21A    FIG. 21B

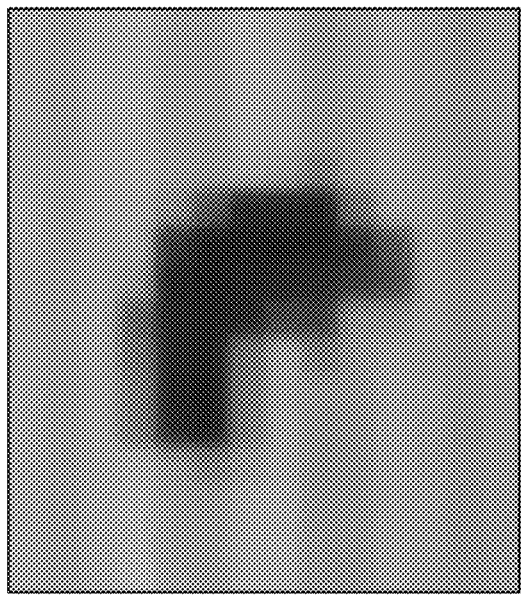 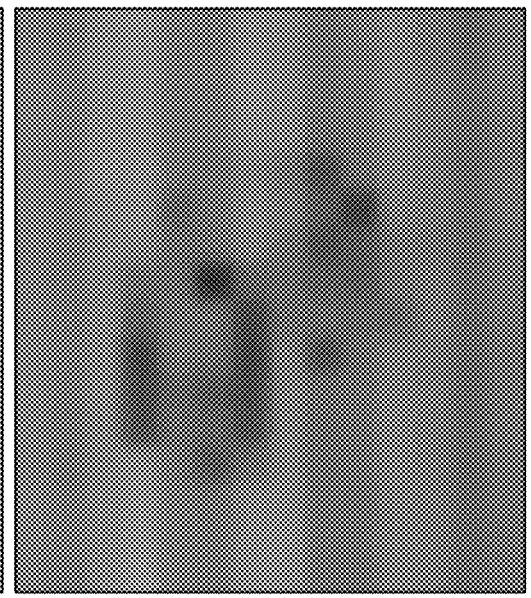
FIG. 22A    FIG. 22B
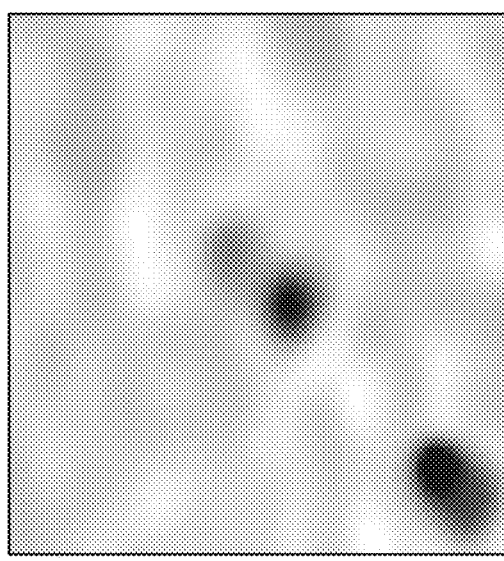 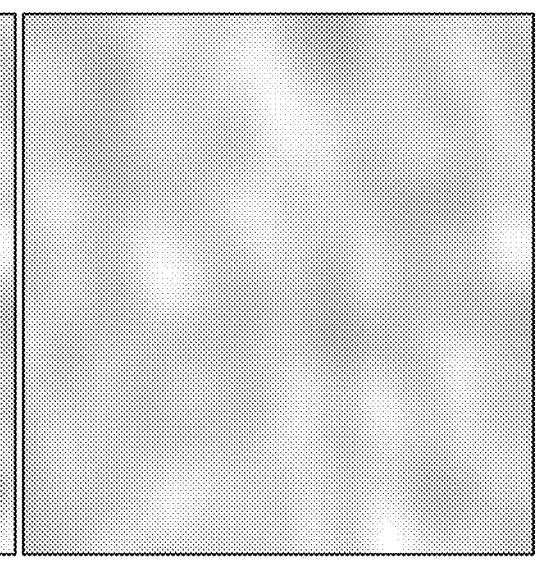
FIG. 23A    FIG. 23B

METHODS, SYSTEMS, AND COMPUTER-READABLE STORAGE MEDIA FOR ENHANCED PHASE-CONTRAST X-RAY IMAGING

ACKNOWLEDGEMENT OF GOVERNMENT SUPPORT

This invention was made with Government support under Contract DE-AC0576RL01830 awarded by the U.S. Department of Energy. The Government has certain rights in the invention.

FIELD

The present disclosure relates to phase-contrast x-ray imaging, and more particularly to phase-contrast x-ray imaging having improved quality and material discriminating power.

BACKGROUND

X-ray based imaging is used in a variety of non-destructive examination (NDE) applications. In many of these applications, which can range from medical imaging to security screening, the primary x-ray characteristics are density and effective atomic number derived from multi-spectral x-ray attenuation measurements. The addition of phase contrast as a third imaging characteristic can improve material discrimination by detection of refractive and scattering effects in examined objects. However, unwanted spectral effects, misleading image artifacts, and the demands associated with producing images with increased material penetration required novel solutions in order to improve resultant x-ray images. Such solutions are described herein.

SUMMARY

Disclosed are methods, systems, and non-transitory, computer-readable storage media storing programs for phase-contrast x-ray imaging having improved quality and material discriminating power.

In some embodiments, a method comprises emitting source x-rays from a polychromatic source operating at an endpoint energy greater than or equal to 100 keV and generating a spot size greater than or equal to 0.5 mm; creating a series of periodically repeating apparent sources from the source x-rays using a source grating; patterning the series of periodically repeating apparent sources into a patterned beam using an object grating placed proximal to an object to be imaged and at distances $L_1$ from the source grating and $L_2$ from a detector grating, wherein the periodicities, P, of the source and object grating elements are related by $P_{source}=P_{object}*[(L_1+L_2)/L_2]$ and wherein the source and object grating elements are substantially parallel; acquiring through the detector grating a first image with the object and a second image without the object, wherein the detector grating is oriented substantially orthogonally relative to the object grating and beam axis and wherein the object grating and the detector grating have a substantially equivalent x-ray attenuating factor; measuring visibilities of the object grating from the first and second images to determine an object grating visibility reduction due to scatter and beam hardening; measuring visibilities of the detector grating from the first and second images to determine a detector grating visibility reduction due to beam hardening; and applying a beam hardening correction based on a comparison of the object grating visibility reduction and the detector grating visibility reduction to generate a corrected scatter image.

In certain embodiments, the method can further comprise operating the polychromatic source at an endpoint energy greater than or equal to 150 keV, 160 keV, 175 keV, 200 keV, or 450 keV. In certain embodiments, the method can further comprise tilting the object grating and detector grating by rotating the gratings about an axis parallel to grating element lines. In certain embodiments, the method can further comprise tilting the source grating by rotating the gratings about an axis parallel to grating element lines.

In certain embodiments, the object grating is approximately equidistant between the source and the detector. In certain embodiments, the detector grating has a periodicity, $P_{detector}$, equivalent to that of the source grating, $P_{source}$. In certain embodiments, the object and detector gratings comprise an equivalent material and have an equivalent thickness. In certain embodiments, the source grating, object grating, detector grating, or combinations thereof have grating elements comprising a parallel line pattern.

In certain embodiments, the object to be imaged is a scatter test object calibration standard and further comprising performing a calibration of x-ray scatter, the scatter test object calibration standard comprising metal or metal oxide particles distributed in a polymer matrix and having a stepped-wedge geometry of at least three different thicknesses. In certain embodiments, the object to be imaged is a beam hardening test object calibration standard and further comprising performing a calibration of beam hardening, the beam hardening test object calibration standard comprising three or more homogeneous materials in a range of atomic numbers, with no large density variations on length scales between 10 nm and 200 microns, and have a thickness such that 10-90% of the x-ray intensity is transmitted through the test object.

In some embodiments, a system comprises a polychromatic x-ray source configured to provide source x-rays at an endpoint energy greater than or equal to 100 keV and a spot size greater than 0.5 mm; a source grating configured to create a series of periodically repeating apparent sources from the source x-ray; an object grating proximal to a position of an object to be imaged and at distances $L_1$ from the source grating and $L_2$ from a detector grating, wherein the periodicities of the source and object gratings are related by $P_{source}=P_{object}*[(L_1+L_2)/L_2]$, the object grating configured to pattern the series of periodically repeating apparent sources into a patterned beam; and a detector grating having detector grating elements that are oriented orthogonally relative to object grating elements and a beam axis, the detector and object gratings having an equivalent x-ray attenuation factor. The system further comprises processing circuitry operably connected to the detector and configured to execute computer-readable instructions to acquire through the detector grating a first image with the object and a second image without the object; measure visibilities of the object grating from the first and second images to determine an object grating visibility reduction due to scatter and beam hardening; measure visibilities of the detector grating from the first and second images to determine a detector grating visibility reduction due to beam hardening; and apply a beam hardening correction based on a comparison of the object grating visibility reduction and the detector grating visibility reduction to generate a corrected scatter image.

In certain embodiments, the polychromatic source is configured to provide source x-rays at an endpoint energy greater than or equal to 150 keV, 160 keV, 175 keV, 200 keV, or 450 keV. In certain embodiments, the object grating and detector grating are positioned such that object grating elements and detector grating elements are tilted by a rotation of the gratings about an axis parallel to grating element lines. In certain embodiments, the source grating is positioned such that source grating elements are tilted by a rotation of the gratings about an axis parallel to grating element lines. In certain embodiments, the object grating is positioned approximately equidistant between the source and the detector. In certain embodiments, the detector grating has a periodicity, $P_{detector}$, equivalent to that of the source grating, $P_{source}$. In certain embodiments, the detector grating abuts the detector. In certain embodiments, the object and detector gratings comprise an equivalent material and have an equivalent thickness. In certain embodiments, the source grating, object grating, detector grating, or combinations thereof have grating elements comprising a parallel line pattern.

In some embodiments, a non-transitory computer readable storage medium stores one or more programs, the one or more programs comprise instructions, which when executed by one or more processors operably connected to an x-ray imaging system, cause the system to acquire through the detector grating a first image with the object and a second image without the object; measure visibilities of the object grating from the first and second images to determine an object grating visibility reduction due to scatter and beam hardening; measure visibilities of the detector grating from the first and second images to determine a detector grating visibility reduction due to beam hardening; and apply a beam hardening correction based on a comparison of the object grating visibility reduction and the detector grating visibility reduction to generate a corrected scatter image. The x-ray imaging system to which the processor(s) are operably connected comprise a polychromatic x-ray source configured to provide source x-rays at an endpoint energy greater than or equal to 100 keV and a spot size greater than 0.5 mm; a source grating configured to create a series of periodically repeating apparent sources from the source x-ray; an object grating proximal to a position of an object to be imaged band at distances $L_1$ from the source grating and $L_2$ from a detector grating, wherein the periodicities of the source and object gratings are related by $P_{source} = P_{object} * [(L_1 + L_2)/L_2]$, the object grating configured to pattern the series of periodically repeating apparent sources into a patterned beam; and a detector grating having detector grating elements that are oriented orthogonally relative to object grating elements and a beam axis, the detector and object gratings having an equivalent x-ray attenuation factor.

In certain embodiments, the non-transitory computer readable storage medium storing one or more programs, the one or more programs comprising instructions, which when executed by one or more processors operably connected to the x-ray imaging system further cause the x-ray imaging system to perform a calibration, wherein the object to be imaged is a scatter test object, a beam hardening test object, or both.

The purpose of the foregoing summary and the latter abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. Neither the summary nor the abstract is intended to define the invention of the application, which is measured by the claims, nor is it intended to be limiting as to the scope of the claims in any way.

BRIEF DESCRIPTION OF THE DRAWINGS

FIG. 11A is a photograph of ZnO scatter step wedge calibration standards. FIG. 11B are beam-hardening corrected scatter images taken at high energy (160 kV with 2 mm Cu and 2 mm Al filtration) and at low energy (100 kV with 2 mm Al filtration).

FIGS. 18A and 18B are (18A) close-up of a region of the grating image, showing the vertical grating lines and the longer period Moire pattern. Near the center is a line of bad pixels from a scratch on the detector and (18B) close up of a grating image with both the object and detector gratings, in a section of bad pixels.

FIGS. 19A-19C are regions of a Fourier transform of a grating image.

FIG. 20 is a Fourier transform of a grating image with both an object and detector grid, showing first and second harmonics as well as cross-harmonics.

FIGS. 21A and 21B are images before and after bad pixel correction of a line of bad pixels, respectively.

FIGS. 22A and 22B are images before and after bad pixel correction of a blob, respectively.

FIGS. 23A and 23B are images before and after bad pixel correction of a scatter image of a region illustrated in FIG. 21A.

DETAILED DESCRIPTION

Figure 1A:
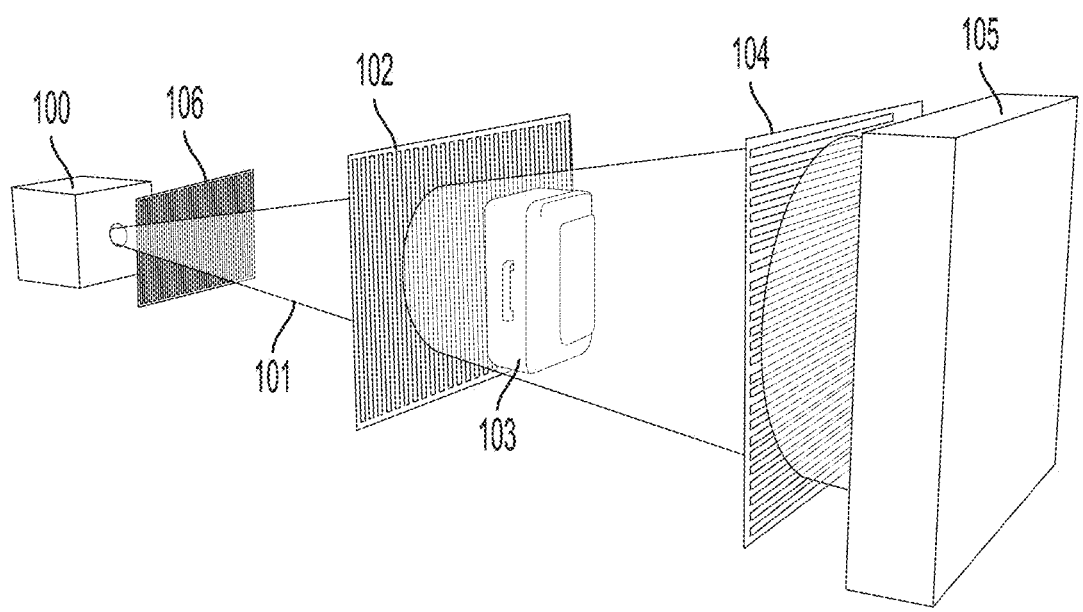
FIGS. 1A and 1B include a schematic diagram and a flow chart, respectively, depicting embodiments described herein.

Phase contrast x-ray imaging or gratings-based phase contrast imaging can allow for detection of small deviations in the direction of an x-ray as it passes through a material. These deflections, specifically scatter, can be used to detect texture in a material, such as a powder or a composite, below the imaging resolution of the system. The inventors have determined that measurements at high energies can provide scatter signatures indicative of sub-resolution texture within a sample in order to help identify materials and that the systems, methods, and storage media described herein can be relevant for applications ranging from medical imaging to materials characterization to security screening.

Embodiments described herein can be utilized for discernment of materials properties, especially in non-destructive examination applications. For example, material wetting or compression could be examined (e.g., concrete, plaster, materials that are formed through compression of powders), as could fiber orientations in materials made from carbon fibers or other fibrous materials. Medical applications are also possible, including diagnostic imaging with either radiography or CT. Scatter has been shown to give enhanced contrast for lung structure and for bones. Finally, additional security screening applications may be possible, such as detecting 3-D fabricated parts based on texture or locating powdered materials in mail screening or vehicle screening. Conventional airport security relies on dual-energy x-ray images that can be used to estimate material density and effective atomic number; these two features are relied upon to discriminate threat objects from benign consumer products. However, the estimation from conventional security scanners is often insufficient to effectively distinguish and identify threat objects. Phase contrast imaging can provide additional materials signatures from x-ray measurements: attenuation, which is similar to a conventional x-ray image; refraction or phase, which is based on electron density variations and can be sensitive to low-Z materials; and scatter, which detects the presence of texture (such as powders or composites) below the imaging resolution of the system. The addition of new signatures increases the number of features which can be used for material discrimination, potentially reducing false alarm rates during security screening. Furthermore, one mode may have a lower detection limit than absorption, enabling the detection/identification of additional items and/or features.

Current phase contrast imaging systems typically rely on a grid which produces an x-ray interference pattern (typically with a period of a few microns) and an analyzer grid matched to the undistorted interference pattern. These systems require sub-micron stability and are very difficult to scale to higher, more penetrating energies; they often operate at energies below 100 kVp. When grid fabrication for energies above 100 kVp is possible, it is difficult and expensive. First, the period should be smaller than the coherence length (which decreases as energy increases). Second, the thickness of the attenuating parts of the grid need to be thick enough to stop the x-rays, and this becomes larger at high energies. The net effect is that fabrication with fine feature sizes but extremely large aspect ratios are required; something that is often impractical to manufacture.

For aviation security, phase contrast imaging is not currently used. Dual energy systems provide estimates of material density and effective atomic number to help discriminate benign materials from threats. Adding phase contrast would allow refraction information and texture information to be measured in addition to dual energy, providing a broader basis of material signatures for discriminating materials, and potentially reducing false alarm rates.

Embodiments described herein can detect sub-resolution texture using an object grid as a patterning object in the beam and at a standoff distance from the detector, where the image of the object grid is projected. If a sample containing sub-resolution density variations (such as a powder) is placed near the object grid, the refractive index variations within the object will cause deflections of the x-ray beam, ultimately causing blurring of the projected object grid pattern. This can be described as a reduction in visibility of the pattern.

Importantly, traditional phase contrast imaging occurs at relatively low energies (<100 kVp). Embodiments described herein measure x-ray refraction and scatter at higher energies, while making corrections for spectral effects which can cause spurious scatter-like signals. The embodiments enable the use of high energies which are relevant for NDE applications including airport screening (e.g. 160 kVp). Indeed, the inventors have measured scatter at energies as high as 450 kVp.

The x-ray energies referred to herein are endpoint energies. An x-ray tube produces a polychromatic spectrum of x-rays, with a peak energy defined by the electron energy impinging upon the anode. As the x-rays pass through the object, some energies are more readily absorbed than others, which means that the spectrum behind the object is different than the original spectrum. This in turn changes the visibility of the grid lines. For most materials in the range of energies described herein for x-ray imaging, higher energies are more penetrating than lower energies, which are more readily absorbed in materials. This means that the original visibility of an object grid will tend to be higher for lower energies. When a polychromatic beam passes through an object, the lower energies in the spectrum are more readily absorbed, an effect referred to as "beam hardening". In this case, the inventors have determined that since the resulting spectrum has more intensity at high energy than the original spectrum, this will cause a reduction in the visibility of the object grid, even in the absence of actual scattering in the object. As the system is run at higher energies and used to interrogate more attenuating objects, the changes in beam spectrum caused by object attenuation also lead to changes in grid pattern visibility, which must be corrected for in order to isolate the visibility reduction due to scatter.

Embodiments described herein differ from other three-grid combination systems and methods at least because some embodiments enable high-energy operation using a polychromatic radiography source (e.g., energies above 100 kVp, 125 kVp, 150 kVp, 160 kVp, 175 kVp, 200 kVp, or 450 kVp, with a spot size, defined as the spatial extent of the region on the x-ray tube anode from which x-rays are emitted, of at least 0.5 mm), in contrast to a synchrotron source or a conventional source operated at lower energies and/or spot sizes. In certain embodiments, the source operates with a current ranging from 0.1 to 1000 milliamps.

In particular, embodiments described herein differ from a three-grid Talbot-Lau interferometer, which uses a source grid to increase spatial coherence, an object grid that forms an interference pattern, and an analyzer grid that detects small changes in the very small interference pattern. In other words, the object grid is a phase element and sets up an interference pattern that impinges on the analyzer grid in order to help detect deviations in the interference pattern without resolving it directly. The source grid in the Talbot-Lau configuration is required to form a sufficiently smooth wave front to establish an interference pattern and the required coherence. In contrast, embodiments described herein utilize large spot sizes (at least 0.5 mm) while retaining the ability to not blur the pattern image and to improve resolution, not coherence. The Talbot-Lau analyzer grating is aligned with the object grating and matches the projected object grating period. Another distinction of present embodiments compared to a Talbot-Lau-style interferometer is the absence of a requirement for gratings which are both fine (period of 5 microns or less) and extremely high aspect ratio (often 10:1, and up to 100:1 for 100 keV), sub-micron alignment and stability, and highly precise (sub-micron) stepping of an analyzer grid placed near the detector. This combination is difficult and impractical for many applications for conventional systems. In contrast, some embodiments described herein utilize gratings having grating elements comprising parallel channels with an aspect ratio less than 10:1, 8:1, 5:1, or 3:1 when the source operates at an energy of at least 100 kVp. In certain embodiments, the gratings can have a scale greater than a 2 micron period, a 5 micron period, a 10 micron period, a 25 micron period, a 50 micron period, or a 100 micron period, which can enable different fabrication methods that are much easier.

In summary, the inventors have determined that the combination of a directly imaged, attenuation-based object grid, the use of a source grid to improve imaging of the object grid using a high-energy polychromatic source with a large spot size, and the use of a stationary detector grid having gratings oriented substantially orthogonally to that of the object grid, addresses the artifacts and beam hardening effects that limit the quality and discriminatory power of high-energy x-ray imaging that includes phase contrast. The object grid is visible on the detected image and is, therefore, sufficiently coarse to be directly visualized on the detector. However, this coarseness can reduce scatter sensitivity. In certain embodiments, the object grid is positioned substantially equidistant between the source and detector in order to optimize contrast for most samples by providing 2× magnification of the grid on the detector. Furthermore, most high energy sources have a large x-ray tube spot size, so their use is enabled by the added source grid. Finally, high energy applications typically involve highly attenuating objects, making the beam hardening correction critical for accurate results, which requires the detector grid. Thus, all three grids operate synergistically to enable embodiments disclosed herein.

The explanations of terms and abbreviations herein are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, distances, energies, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximations unless the word "about" is recited.

Referring to FIG. 1A, a diagram summarizes one embodiment of a system for beam-hardening-corrected, phase-contrast, x-ray imaging. As illustrated, the embodiment comprises three x-ray anti-scatter grids having parallel line grating elements. The source grid 106 is placed at the x-ray source 100, the object grid 102 is in proximity to an object 103 being imaged, and the detector grid 104 abuts the detector 105. The source and detector are placed some distance apart, with an object being imaged located between the source and the detector. The source is operated at high energies and generates a large spot size. The object grid can be on the source or detector side of the object and the object grid lines are spaced at period, $P_{object}$. The source grid is placed near the x-ray source with period, $P_{source}$ substantially equal to $P_{object} \cdot [(L_1+L_2)/L_1]$, wherein $L_1$ and $L_2$ are distances from the source to the object and from the object to the grid, respectively. In certain embodiments, the distance between the source and the object and the distance between the object and detector are substantially equivalent. In certain embodiments, the detector grating has a periodicity that is equivalent to that of the source grating. The fundamental relationship is between $P_{source}$ and $P_{object}$, to get the patterns to overlay when projected onto the detector. As a matter of convenience, efficiency, and/or optimization to set $P_{detector}$ equal to the projected $P_{object}$ to make the regions around their respective Fourier peaks are about the same size in Fourier space. When $L_1$ and $L_2$ are equal, $P_{source}$ can equal $P_{detector}$.

The source grid can compensate for a large x-ray tube spot size, which can be detrimental to being able to resolve the lines of the object grid. In other words, the source grid can allow the object grid to be imaged on the detector more clearly. The detector grid is placed at the detector and the orientation of the grating elements is substantially 90 degrees rotated relative to those of the object grid. With regard to rotation of the detector grating elements, substantially can refer to an error of ±1, ±2, or ±5 degrees. In certain embodiments, the error in detector grating rotation angle should be less than that which would avoid overlap of the first harmonics in Fourier space.

The object grid and detector grid have substantially the same attenuating factor. With regard to the attenuating factor, substantially refers to an error of ±1%, ±3%, ±5%, or ±10%. For example, the object and detector grids can comprise the same material and same thickness. The detector grid is used to correct for artifacts caused by beam hardening, where the spectrum of the beam is changed by attenuating objects. When the object grid is substantially equidistant from the source and detector, the source and detector gratings can have substantially the same grating element period.

Figure 1B:
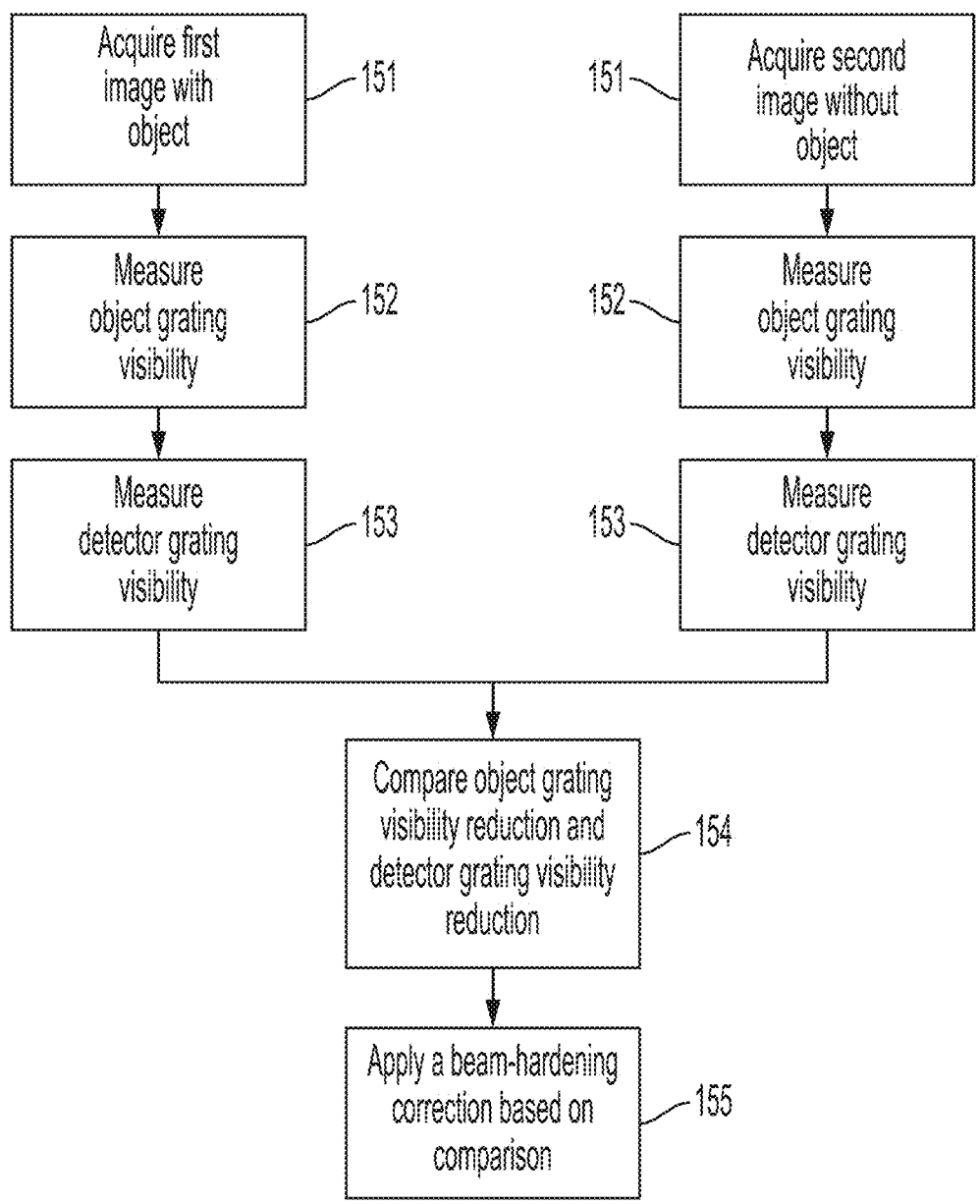

FIG. 1B includes a flowchart summarizing one example of a computer-implemented method of beam-hardening correction of phase-contrast x-ray imaging. The method can be embodied by non-transitory, computer-readable storage media storing instructions that can be executed to perform the method. In the illustrated example, first and second images are acquired with and without the object to be imaged 151. The "first image" and "second image" terms do not refer to chronological sequence; the images can be acquired in any order. The object grating visibilities are measured in both images 152. Similarly, the detector grating visibilities are measured in both images 153. The visibilities are compared 154 to determine the object grating visibility reduction and the detector grating visibility reduction. Based on the comparison of the reductions 154, a beam-hardening correction is applied 155 to yield a corrected phase-contrast x-ray image.

Non-transitory as used herein when referring to a computer-readable storage medium, is a limitation of the medium itself (i.e., tangible, not a propagating electromagnetic signal) as opposed to a limitation on data storage persistency. The term is not intended to otherwise limit the type of physical computer-readable storage device that is encompassed by the phrase computer-accessible medium or memory. For instance, the terms "non-transitory computer readable medium" or "tangible memory" are intended to encompass types of storage devices that do not necessarily store information permanently, including but not limited to, computer-readable media that store data only for short periods of time and/or only in the presence of power, such as register memory, processor cache and Random Access Memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

Figure 2:
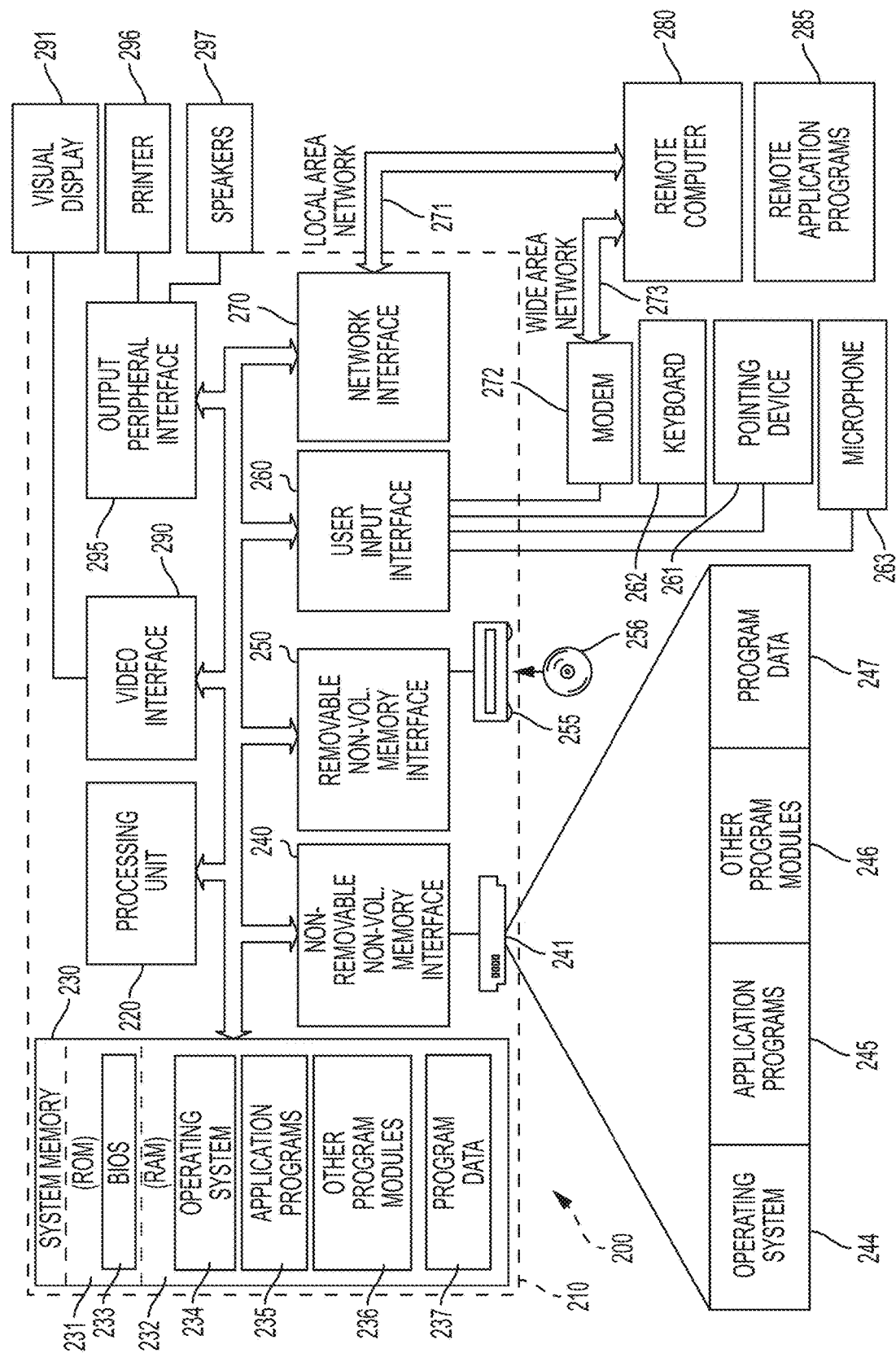
FIG. 2 is a diagram of one embodiment of a computational system for enhanced phase-contrast x-ray imaging and/or beam-hardening correction.

FIG. 2 is one embodiment of a computational system or computing environment to which an enhanced phase-contrast x-ray imaging system can be operably connected. Alternatively, the computational system can be integrated within an enhanced phase-contrast x-ray imaging system. In one example, a computing environment such as shown in FIG. 2 can be used to control operation of the imaging system. The computing environment can further be used to acquire images and to perform beam-hardening corrections as described elsewhere herein.

With reference to FIG. 2, an example system for implementing some embodiments includes a general-purpose computing device in the form of a computer 210. Components of computer 210 may include, but are not limited to, a processing unit 220 (which is not limited to CPUs, but can comprise GPUs), a system memory 230, and a system bus 221 that couples various system components including the system memory to the processing unit 220. The system bus 221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. Memory and programs described herein be deployed in corresponding portions of FIG. 2.

Computer 210 typically includes a variety of computer readable media. Computer readable media can be any available media that can be accessed by computer 210 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, sash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 210. Communication media typically embodies computer readable instructions, data structures, program modules or other data in a transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 230 includes computer storage media in the form of volatile and/or nonvolatile memory such as read only memory (ROM) 231 and random-access memory (RAM) 232. A basic input/output system 233 (BIOS), containing the basic routines that help to transfer information between elements within computer 210, such as during startup, is typically stored in ROM 231. RAM 232 typically contains data and/or program modules that are immediately accessible to and/or presently being operated on by processing unit 220. By way of example, and not limitation, FIG. 2 illustrates operating system 234, application programs 235, other program modules 236, and program data 237.

The computer 210 may also include other removable/nonremovable volatile/nonvolatile computer storage media. By way of example only, FIG. 2 illustrates a hard disk drive 241 that reads from or writes to non-removable, nonvolatile magnetic media, and an optical disk drive 255 that reads from or writes to a removable, nonvolatile optical disk 256 such as a DVD or other optical media. Other removable/non-removable, volatile/nonvolatile computer storage media that can be used in the exemplary operating environment include, but are not limited to, magnetic tape cassettes, sash memory cards, DVDs, digital video tape, solid state RAM, solid state ROM, and the like. The hard disk drive 241 is typically connected to the system bus 221 through a non-removable memory interface such as interface 240, and optical disk drive 255 are typically connected to the system bus 221 by a removable memory interface, such as interface 250.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The drives and their associated computer storage media discussed above and illustrated in FIG. 2, provide storage of computer readable instructions, data structures, program modules and other data for the computer 210. In FIG. 2, for example, hard disk drive 241 is illustrated as storing operating system 244, application programs 245, other program modules 246, and program data 247. Note that these components can either be the same as or different from operating system 234, application programs 235, other program modules 236, and program data 237. Operating system 244, application programs 245, other program modules 246, and program data 247 are given different numbers here to illustrate that, at a minimum, they are different copies.

A user may enter commands and information into the computer 210 through input devices such as a keyboard 262, a microphone 263, and a pointing device 261, such as a mouse, trackball or touch pad. Other input devices (not shown) may include a joystick, game pad, satellite dish, scanner, or the like. These and other input devices are often connected to the processing unit 220 through a user input interface 260 that is coupled to the system bus, but may be connected by other interface and bus structures, such as a parallel port, game port or a universal serial bus (USB). A visual display 291 or other type of display device is also connected to the system bus 221 via an interface, such as a video interface 290. Video interface 290 can comprise a graphics card having a GPU. The GPU be used for computations. In addition to the monitor, computers may also include other peripheral output devices such as speakers 297 and printer 296, which may be connected through an output peripheral interface 295.

The computer 210 is operated in a networked environment using logical connections to one or more remote computers, such as a remote computer 280. The remote computer 280 may be a personal computer, a hand-held device, a server, a router, a network PC, a peer device or other common network node, and typically includes many or all of the elements described above relative to the computer 210. The logical connections depicted in FIG. 2 include a local area network (LAN) 271 and a wide area network (WAN) 273, but may also include other networks. Such networking environments are commonplace in offices, enterprise-wide computer networks, intranets and the Internet.

When used in a LAN networking environment, the computer 210 is connected to the LAN 271 through a network interface or adapter 270. When used in a WAN networking environment, the computer 210 typically includes a modem 272 or other means for establishing communications over the WAN 273, such as the Internet. The modem 272, which may be internal or external, may be connected to the system bus 221 via the user input interface 260, or other appropriate mechanism. In a networked environment, program modules depicted relative to the computer 210, or portions thereof, may be stored in the remote memory storage device. By way of example, and not limitation, FIG. 2 illustrates remote application programs 285 as residing on remote computer 280. It will be appreciated that the network connections shown are exemplary and other means of establishing a communications link between the computers may be used.

EXAMPLES AND COMPARISONS

To further illustrate certain embodiments of the disclosed methods, systems, and computer-readable storage media, and to provide various comparative analyses and data, below are some examples with comparison test data.

Figure 3:
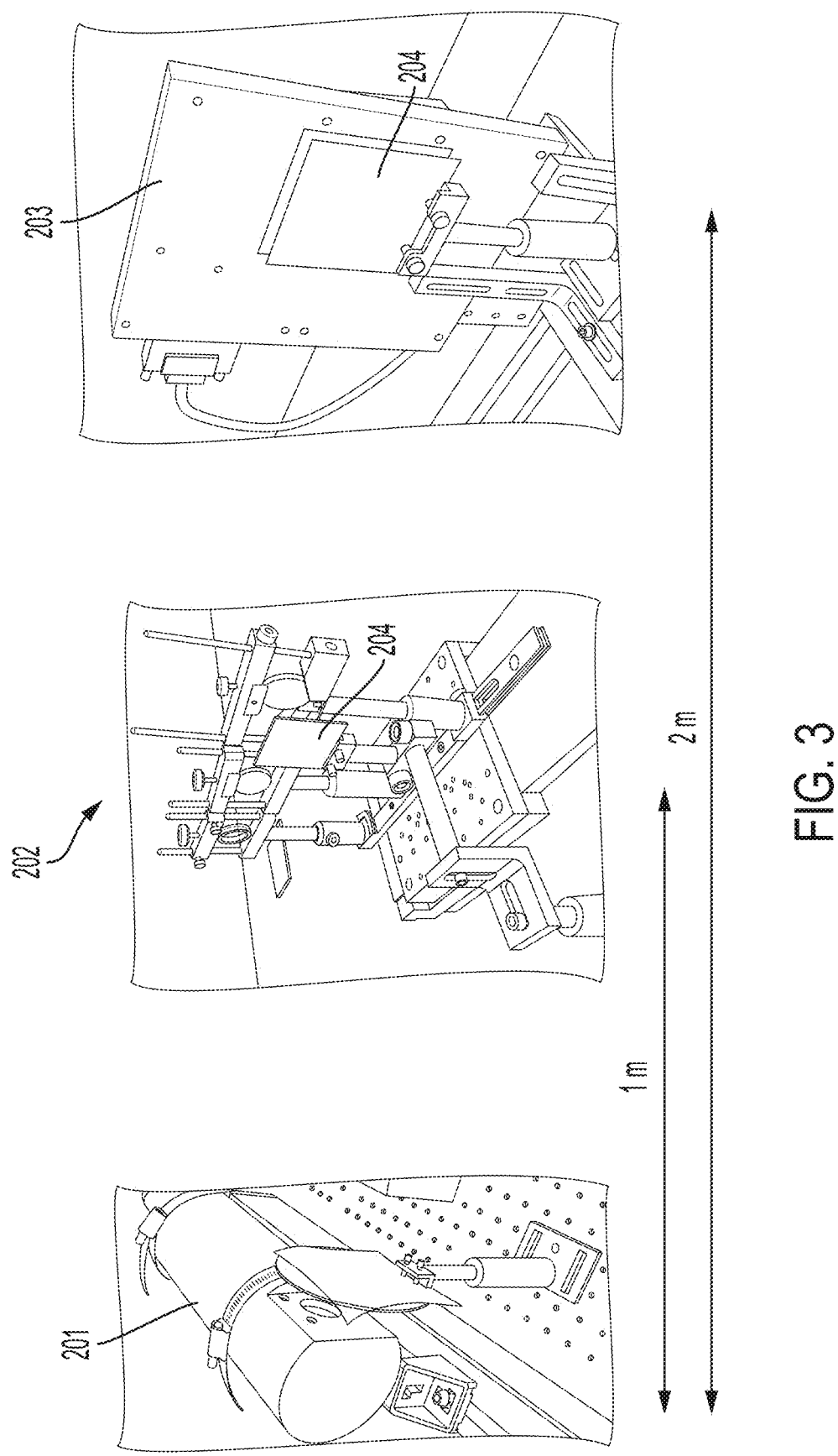
FIG. 3 includes photos of one embodiment of an arrangement of source, object, and detector gratings in an enhanced phase-contrast x-ray imaging system.

Photos of a basic system, including a source, object grid, and detector are shown in FIG. 3. The x-ray source 201 used was a Comet MXR-160HP/11 x-ray tube with a maximum energy of 160 kV. The maximum power was 1800 W with a 1 mm spot size or 800 W with a 0.4 mm spot size. In some embodiments, when the spot size is too large to resolve the object grid on the detector, a source grid is necessary. The relationship describing the spot size above which the ability to resolve the object grating is reduced can be expressed as $w_{source} \geq (L_1+L_2)*P_{obj}/L_2$ where w is the spot size of the source, $L_1$ is the source-to-object distance, and $L_2$ is the object-to-detector distance. Test data shown below used 1 mm Al and 0.1 mm Cu to filter the spectrum of the beam and reduce the flux at very low photon energies. The working distance from source to detector 203 was set at 2 m, and the detector used initially was a CMOS X-ray detector (e.g., Shad-o-box® 4 k) with a 10 cm×10 cm field of view, 48 μm pixel pitch, and a $Gd_2O_2S$:Tb scintillator (Teledyne DALSA®). The object and object grid 202 were placed halfway between the source and detector, resulting in a two-times magnification and good sensitivity to the small angular deflections by the sample. The beam pattern was created with commercial anti-scatter grids 204 used for medical imaging, consisting of parallel line patterns between 85 and 285 lines per inch (LPI). Typically, the grids are made of lead and aluminum sheets interspersed, but the finest grid was made with carbon fiber between lead sheets. A second grid, approximately half the object grid's spatial frequency, was oriented such that the grid lines were perpendicular to those of the object grid and was placed directly in front of the detector in order to correct for beam hardening, as described elsewhere herein.

Figure 4:
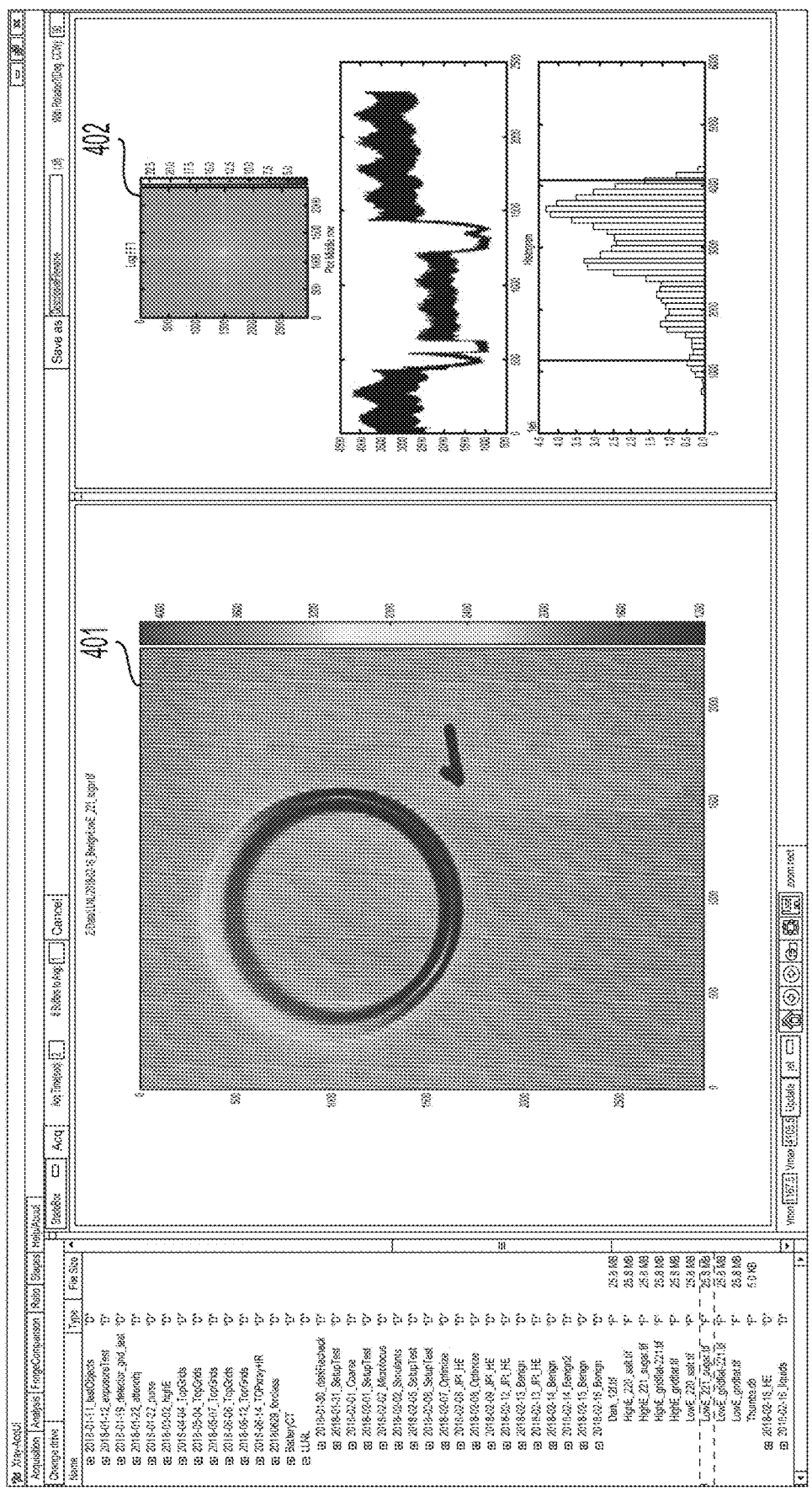
FIG. 4 is a screenshot of one example of image acquisition and processing software.

Custom software was developed to handle both data acquisition and extraction of absorption, phase, and scatter images. Frames were acquired from the detector, summed, and saved as floating-point tiff files; this file type allowed viewing as an image while preserving raw numbers from the detector and the full bit-depth of the detector. The interface to the data acquisition and processing software is shown in FIG. 4.

Figure 5:
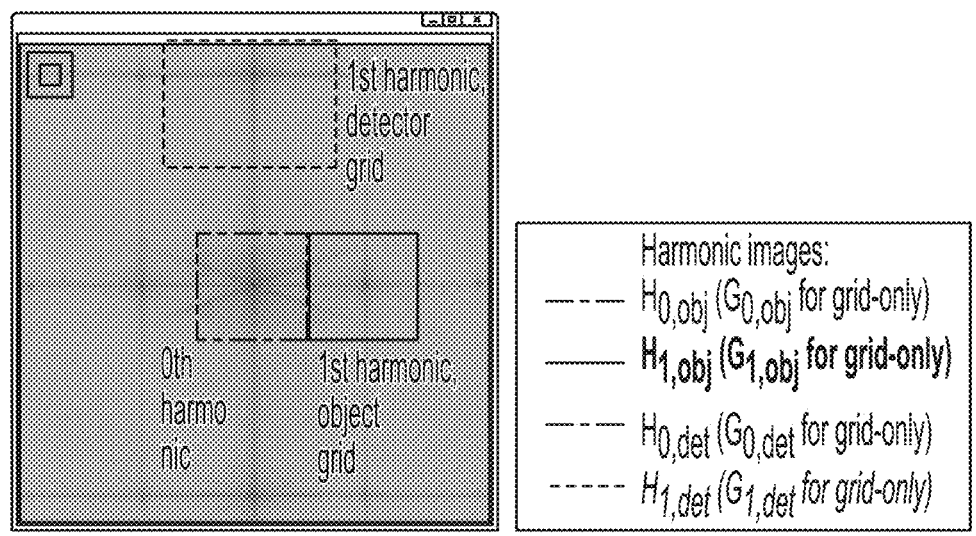
FIG. 5 includes an image of a Fourier transform of an image obtained by enhanced phase-contrast x-ray imaging as described herein.

Raw images 401 resembled a normal attenuation image, but with fine vertical and horizontal lines visible from the object and detector grids. A Fourier-based processing method was used. First, a Fourier transform 402 is taken of the image. For a system with parallel line grids, peaks will be visible in the Fourier transform corresponding to the spatial frequency of the grid. In FIG. 5, peaks to the right and left of center correspond to the first harmonic associated with the object grid (which was oriented with its grid lines vertical), and the peaks at top and bottom are the first harmonic of the detector grid (which was oriented with its lines horizontal. The region around the first harmonic when an object is present is compared with the same region a grid-only image (no sample). Pattern displacements of the object grid were determined based on the phase values in a region of the Fourier transform around the first harmonic. These were interpreted as refraction and formed the differential phase contrast image. Pattern visibility, V, is calculated based on the ratio of the inverse Fourier transform of the region around the first harmonic to the inverse Fourier transform of the region around the zeroth harmonic, but can be more simply understood as the amplitude of the projected grid pattern divided by the mean. Pattern visibility reduction, $V/V_0$, which compares pattern visibility with an object present to pattern visibility without, was interpreted as scatter. Note, visibility can be reduced not only by scattering effects but also by beam hardening, since a harder spectrum may result in less modulation of the object grid. To correct for this, a detector grid was chosen that has similar attenuation properties as the object grid so that it would be similarly affected by beam hardening. This grid was placed as close as possible to the detector to minimize the effects of scatter on the projected pattern. The ratio of the scatter image to the apparent scatter in the detector grid image produced a correction to remove the portion of the visibility loss due to beam hardening.

Figure 6:
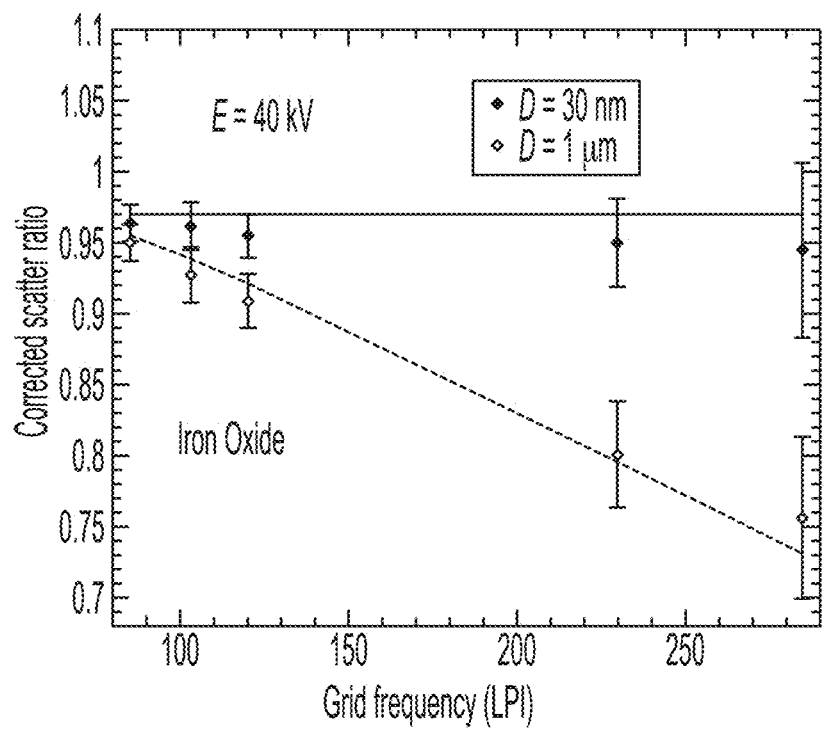
FIG. 6 is a graph showing corrected scatter ratio as a function of grid frequency (in LPI) for two different particle sizes.

The first study performed was a test of the system sensitivity to the object grid spatial frequency. Calibration standards were constructed of iron oxide (i.e., $Fe_3O_4$) nanoparticles dispersed in epoxy at a 20% volume fraction. Objects were 6 mm thick and were constructed with two different sizes of particles: 30 nm and 1 μm. A source spectrum with a peak energy of 40 kV was used. Results are shown in FIG. 6, which shows the corrected scatter ratio, which is the visibility reduction at the object grid after correcting for beam hardening as a function of grid frequency (in lines per inch). For the 1 mm particle sample, as the grid frequency was increased, the scatter increased approximately linearly. For the 30 nm particles, the response was independent of grid frequency. This is consistent with theoretical descriptions of the measurement process where the x-ray interactions are due to Small Angle X-ray Scattering (SAXS) and the response of the system is characterized by a parameter known as the correlation length. Thee correlation length of the measurement at 40 kV ranges between 50 and 300 μm depending on the grid frequency. For particles much larger than the correlation length, scatter signal increases with larger grating spatial frequencies, while for samples much smaller than the correlation length, scatter signal should be independent of gratings frequency.

Figure 7:
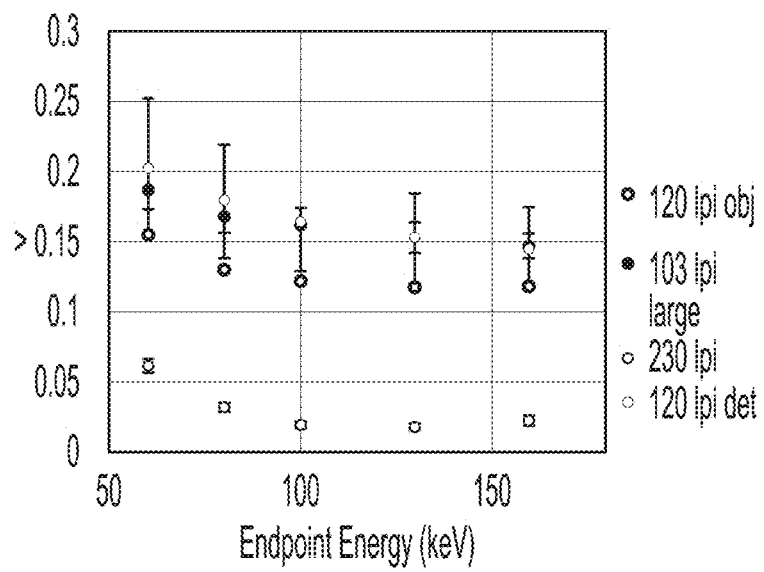
FIG. 7 is a graph showing fringe visibility as a function of endpoint energy and grid spatial frequency.

For explosives detection, particles larger than the correlation length are of primary interest. In certain embodiments, texture is considered to be in the 1-1000 microns for what is defined as a powder. The correlation length is inversely proportional to energy, so increasing the spatial frequency of the object grid as much as possible will improve measurement sensitivity. For signatures of explosive and benign materials that, when textured, typically have variations on length scales ranging from microns to millimeters in size, a finer object grid (higher spatial frequency) is generally advantageous. However, as grid frequency decreases, imaging the projected grid pattern becomes more difficult. This can be caused by the finite size of the x-ray source region in the tube, finite resolution at the detector, and by limited attenuation in a finely patterned grid (as spatial frequencies increase. Therefore, higher aspect ratio fabrication is required in order to retain sufficient thickness to modulate the beam). To examine these effects, we measured the visibility with no object present for several grids and measurement geometries. Higher visibilities indicate a larger fraction of the beam intensity is available for detecting refraction and scatter; lower visibilities will lead to noisier measurements. FIG. 7 is a graph that shows visibility as a function of endpoint energy for 103, 120, and 230 LPI grids placed halfway between source and detector, and a 120 LPI grid placed near the detector. Overall visibility values range from less than 0.05 up to 0.30. Visibility decreases with energy, as the beam becomes more penetrating, but changes relatively slowly at higher energies. The coarsest grid, at 103 LPI, showed the highest visibilities and the finest grid, 230 LPI, showed the lowest. For the 120 LPI grid, measurements were done with the grid halfway between source and detector, where pattern visibility was equally sensitive to resolution limitations due to the source and to the detector, and with the grid near the detector, where resolution was strongly dependent on the detector and independent of the source spot size. The grid showed higher visibility at the detector position, indicating that for grids halfway between source and detector, the source spot size was the dominant factor in reducing visibility.

Figure 8:
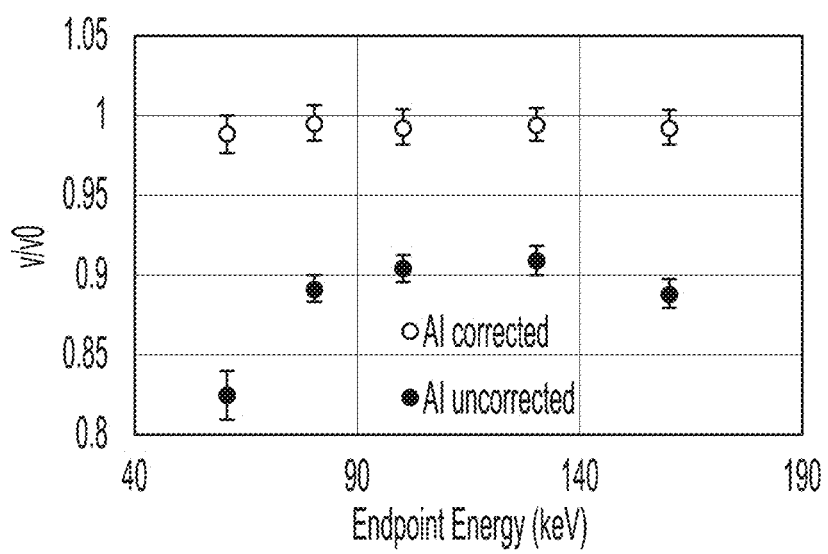
FIG. 8 is a graph showing visibility reduction as a function of endpoint energy, for a 1.26 cm Al sample (shown with and without the beam hardening correction).

The beam hardening correction was tested as a function of energy using a 1.26 cm thick section of aluminum (for reference, the mean free path for attenuation in Al ranges from 0.68 cm at 40 keV to 2.7 cm at 160 keV). This was selected as a material that was expected to be homogeneous over any texture length scales that the measurement would be sensitive to (e.g., nm to μm). Fringe visibility reduction ($V/V_0$, where $V_0$ is the grid visibility without an object present) is plotted in FIG. 8 as a function of endpoint energy, both for the object grid alone (Al uncorrected), and for the object grid after beam-hardening correction by the detector grid (Al corrected). We can verify that, although the raw object grid (uncorrected) shows substantial decreases in fringe visibility, particularly at low energies, the correction by the detector grid results in calculated visibility reduction numbers independent of peak energy and consistent with a ratio of 1, indicating a homogeneous, non-scattering material, as expected.

Figure 9:
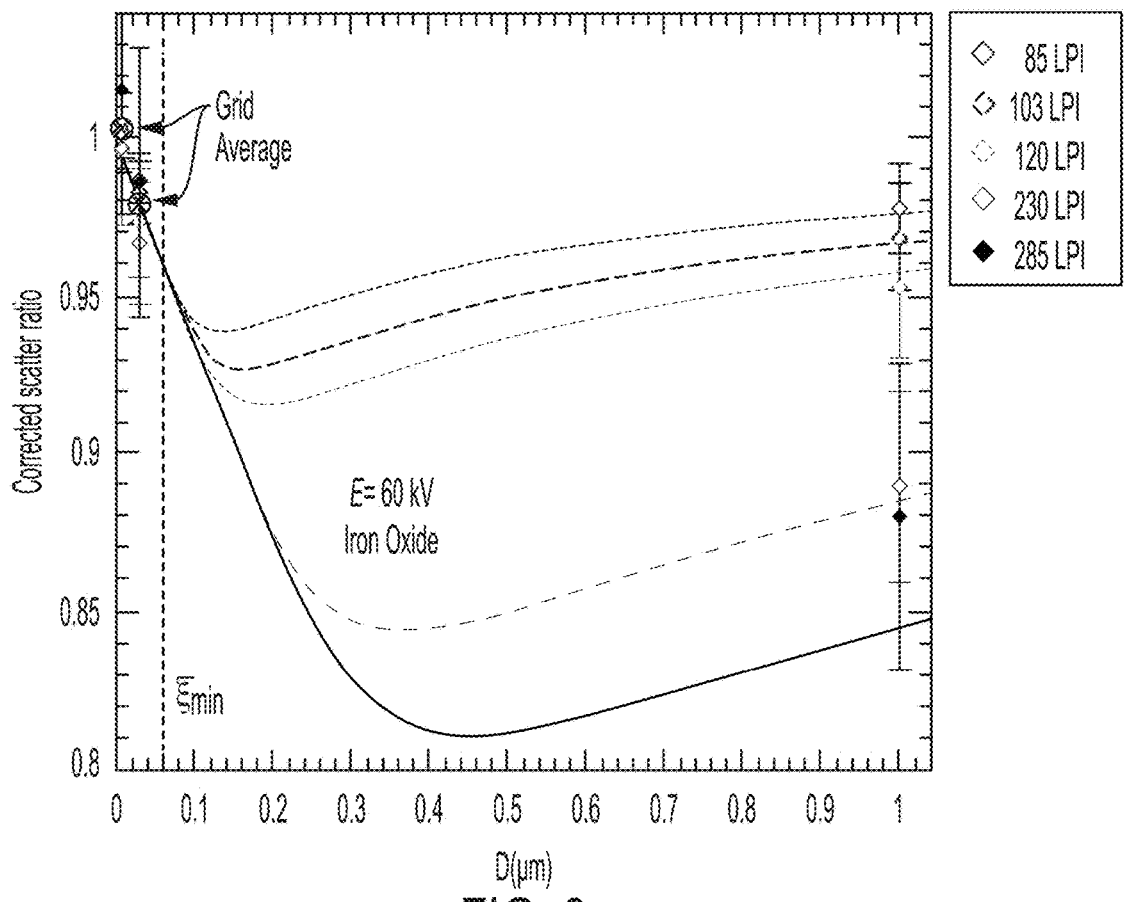
FIG. 9 is a graph showing corrected scatter ratio as a function of particle size, for a 60 kV spectrum. Theoretical predictions are shown as solid lines; measurements are indicated as points with error bars FIGS. 10A and 10B include images of a small bag (8"×9") as in a security screening context.

The scatter for a typical gratings-based setup is expected to be dominated by small angle x-ray scattering (SAXS), a mechanism for elastic scattering that produces a spectrum as a function of a scattering vector reflecting the distribution of spatial features in the sample. For the gratings-based measurement, results are not resolved as a function of scattering vector, but sensitivity is greatest near the scattering angle defined by the object grid-to-detector distance, d, and the size of the projected grid period, $P_{projected}$. The momentum transfer associated with this scattering angle can be related to a correlation length in the material, $\xi_{corr}=d*hc(P_{projected}\cdot E)$, where E is the photon energy and E/hc is the photon wavelength; this correlation length is closely related to the particle size that produces peak scatter intensity. In FIG. 9, we plot corrected scatter ratio as a function of particle size for a 60 kV spectrum. Solid lines are theoretical estimates for a range of grating frequencies. As grating frequency was increased, the effects on scatter ratio become larger, and the correlation length increased as well, leading to peak scattering at increasingly large particle size. Measured results are shown for iron oxide nanoparticles at 7 nm, 30 nm, and 1000 nm mean particle size; they were generally consistent with theoretical predictions.

The measurements shown established that fringe visibility is possible at energies up to 160 kV and illustrated the importance of correcting for beam hardening in interpreting fringe visibility reduction as scatter. A tradeoff is demonstrated between increased scatter signal for higher spatial frequency grids and reduced overall visibility as grid frequency is increased, which will lead to lower signal-to-noise.

A source grid can improve the ability to resolve the object grating. The source grid is aligned parallel to the object grid, with half the spatial frequency (when the object grid was placed substantially equidistant between the source and detector); this results in multiple projected images of the object grid that overlay at the detector. For a 160 kVp spectrum and a 1 mm source spot size, adding a source grid with 50% duty cycle and a period of 4.7 lines per mm increased the visibility of a 9 lines per mm object grid placed 1 m downstream of the source and 1 m upstream of the detector by approximately 4×. This approach allows the use of a larger spot size and therefore higher flux.

Figures 10A, 10B:
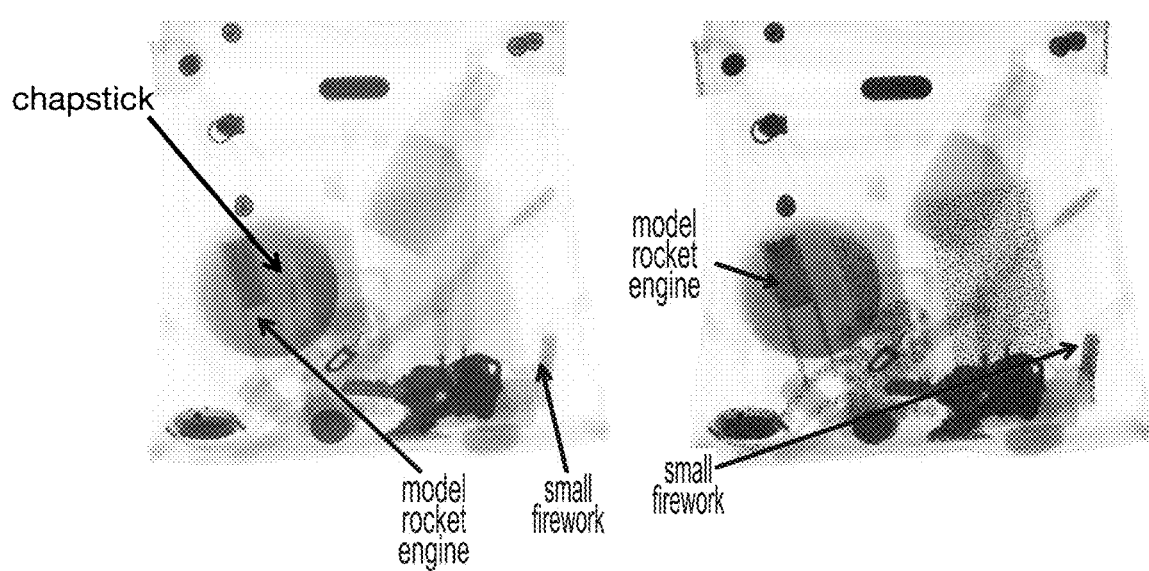
FIG. 10A is a conventional attenuation image.
FIG. 10B is an attenuation image with corrected scatter overlay according to embodiments described herein. Propellants present in the bag show scatter, as do business cards, a watch band, and tic tac candies. Chapstick next to the model rocket engine looks similar by shape, but does not exhibit scatter.

Referring to FIG. 10, a composite image of a small bag (8"×9"), taken at 160 kV using a large spot size and a source grid to improve object grid visibility is shown according to embodiments described herein. The image was acquired using a system comprising a polychromatic source (e.g., Comet x-ray tube) run with a 1 mm spot size, a 103 LPI source grid, 210 LPI object grid, and 103 LPI detector grid oriented perpendicular to the other two for beam hardening corrections, used with the CMOS detector. The image on the left is an attenuation image. The image on the right is an attenuation image with scatter overlay (color). Propellants present in the bag show scatter, as do business cards, a watch band, and tic tac candies. Chapstick next to the model rocket engine looks similar by shape, but does not exhibit scatter.

In order to characterize the performance and verify consistency of an imaging system, particularly the ability to detect texture, a set of calibration standards was developed. The first type of calibration standard comprises a scatter test object and provides a stable and repeatable means for measuring scatter signal across different systems. The inventors determined that the scatter test object, which was stable and robust with well characterized small-scale structure, was beneficial so that the efficacy of different x-ray systems could be tested. The scatter test object can have sufficient contrast for use at high energies, when the cross section for elastic scatter is relatively small. One embodiment of the scatter test object calibration standard comprises a block of polymer with microparticles or nanoparticles dispersed evenly within it. The particles can comprise metal and/or metal oxide. The particles have a known size distribution. The polymer block can be fabricated with a series of steps or geometric features of different thickness. The resulting object provides a measure of x-ray scattering as a function of thickness, over a wide range of imaging systems and x-ray energies, and which is stable and robust. The testing and calibration can be particularly advantageous for certain applications including explosives detection and medical imaging. In such applications, the scatter test object can comprise a scatter-imaging phantom. The phantom is an object having the same scatter qualities and/or properties as a material in which one is interested in imaging.

Figure 11A:
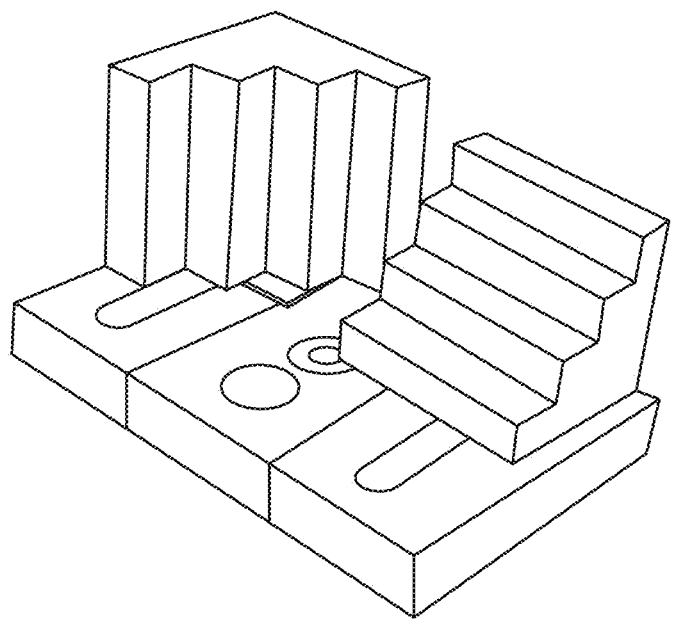
FIGS. 11A and 11B are images related to one embodiment of a calibration standard.
Figure 11B:
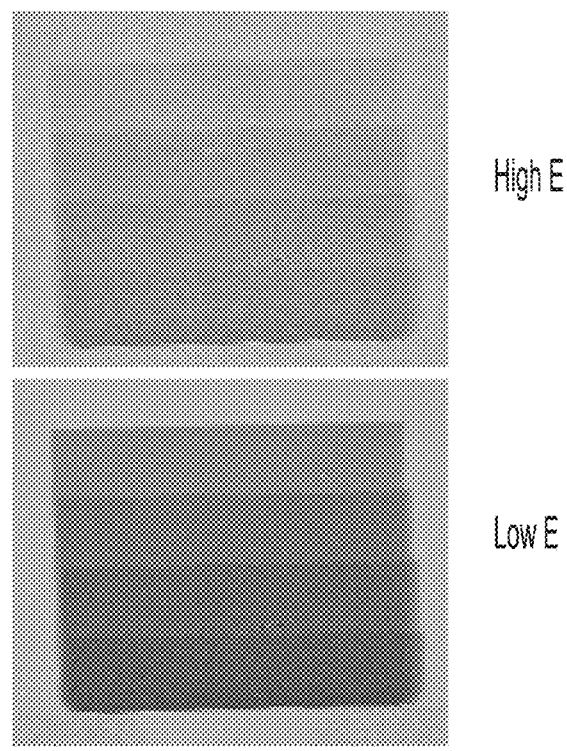

In some embodiments, metal or metal oxide microparticles or nanoparticles were fixed in a polymer. Particles with a well-defined size distribution are commercially available. This is important because the scatter signal exhibits sensitivity to the size of the particles or texture. A polymer (e.g., epoxy) is robust and stable over time and adds no additional scatter signal. The metal or metal oxides have a sufficiently high density that the x-ray refractive index change between the particles and the polymer produce a strong scattering signal. After testing numerous metal and metal oxide nanoparticles and microparticles, ZnO was found to disperse evenly in epoxy, and scatter step-wedges were created out of 20 vol % ZnO particles fixed in epoxy. Blocks were created with 1 µm particles, and with a distribution of particles 5 µm and below; steps were cut to be approximately 6 mm thick with a maximum thickness of 25 mm. The scatter step wedges are shown in FIG. 11A, along with scatter images (see FIG. 11B) at two different energies. When transitioning between different gratings-based systems, or different energies, contrast-to-noise was measured on the step wedges and compared. The scatter test object calibration standard is not limited to a step wedge shape. A wedge with graded thickness is an example of an alternative shape. Further still, the scatter test object can comprise one or more shapes having a constant thickness. A plurality of constant thickness calibration standards, each with different thickness, different particle loadings, and/or particle sizes can be used as an alternative.

Another type of calibration standard comprises a beam hardening test object for phase contrast x-ray imaging, which can be used to test for beam hardening artifacts that can adversely affect the scatter measurement and ensure the artifacts have been properly removed. The use of the beam hardening test object calibration standard relies on the fact that it does not have density fluctuations at length scales to which the measurement is sensitive—that the materials in the calibration standard are homogeneous. This provides a baseline expectation that data taken with the test device will, if properly corrected for beam hardening, indicate no additional fringe visibility loss due to texture. For many applications, a beam hardening correction will be applied for multiple materials, spanning much of the periodic table, and for materials with a wide range of attenuation values. The calibration standard is designed to contain multiple homogeneous materials across a range of atomic number, with the thickness of each material selected so that a moderate amount of attenuation (10% to 90% of the original beam) is present.

One embodiment of the beam hardening test object calibration standard can comprise three or more materials that are each homogeneous, with no large density variations on length scales between 10 nm and 200 microns, and represent a range of atomic numbers. The materials are machined to a thickness suited to the energy of the x-rays used, such that 10-90% of the beam intensity is transmitted through the object. A corrected phase contrast measurement, as described elsewhere herein, is performed with corrections for spurious signals due to spectral changes during attenuation, and the resulting scatter image of the calibration standard will be consistent with background if the correction is successful.

In some embodiments, beam hardening test object comprises approximately one mean free path at 160 kV of aluminum (28 mm), stainless steel (7 mm), copper (5.5 mm), and tin (1.0 mm). This gave a range of Z, and substantial attenuation, over which to test the beam hardening correction. The beam hardening correction can correct partially the visibility reduction observed in the calibration standard materials, in contrast with the complete correction observed with the 12.5 mm Al sample. This appears to be related to the relatively high attenuation of the calibration standard. Known homogeneous material samples (such as water) show a corrected scatter value consistent with homogeneity. Accordingly, there is no issue with the calibration standard significantly impacting the measurements of the explosive and benign materials.

Figure 12:
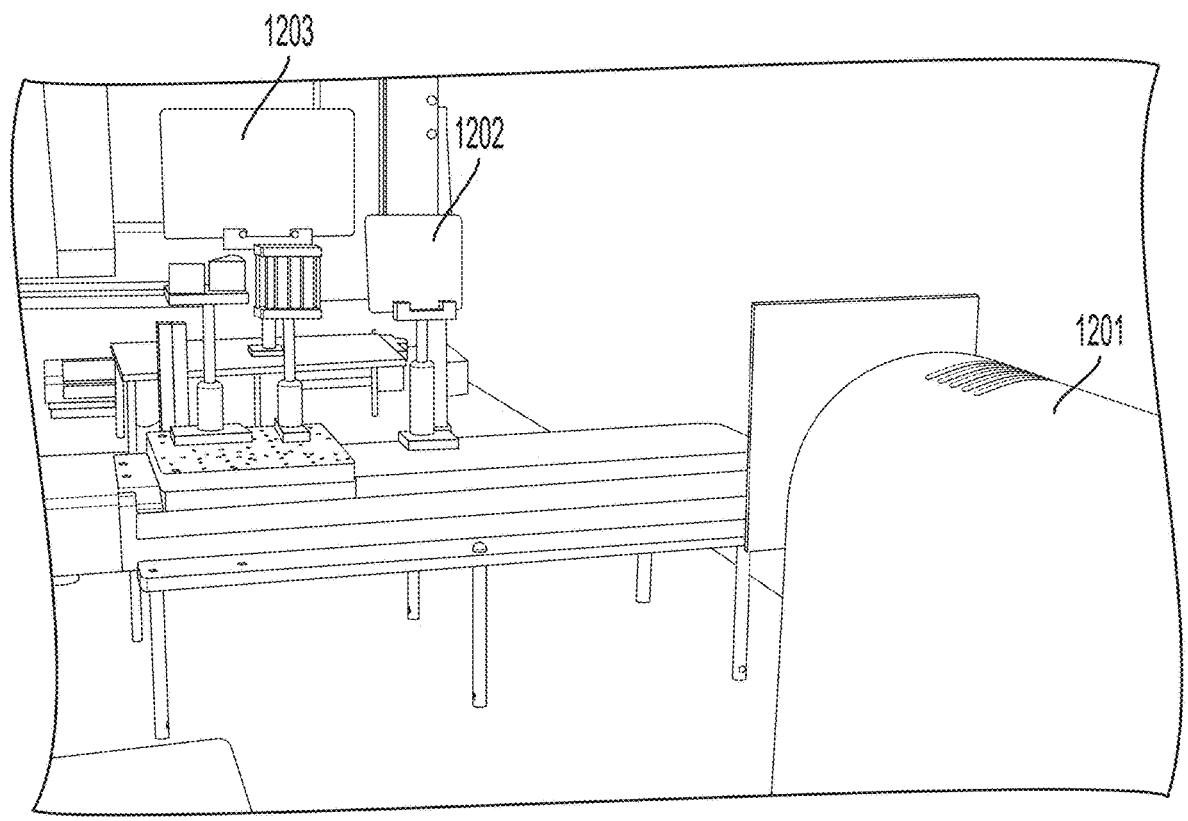
FIG. 12 is a photo of an embodiment of a system described herein (absent a source grid). An X-ray tube is at lower right and the beam direction is from lower right to upper left. Filter materials are immediately in front of the x-ray tube; the standard test objects can be seen halfway down the table at upper left; the object and detector grids are also visible in the upper left quadrant. The detector is obscured by the detector grid.

Measurements of a variety of materials, including threat and non-threat materials, were conducted in collaboration with Chuck Divin, Sabrina De Piero, Larry McMichael, and Harry Martz at Lawrence Livermore National Laboratory. These measurements were performed using a microfocus x-ray tube (Hamamatsu L12161-07). The nominal spot size at max current was 50 µm. The final measurement configuration is shown in FIG. 12 and consisted of the Hamamatsu microfocus tube 1201 operated at 0.5 mA current and 50 µm spot size, an object grid 1202 with 285 LPI (JPI Healthcare), and a detector grid 1203 with 120 LPI (Kiran Medical). Measurement time was necessarily very long—10 minutes, or 300 mA·s. This was selected and verified to be well above the range where noise in the images is dominated by counting statistics, in order to emphasize the physical signatures. The small spot size provided by the microfocus tube necessitated longer measurement times. In some embodiments, high-energy, large spot size measurements described herein have measurement times that are less than 10 minutes, 8 minutes, 6 minutes, 5 minutes, 3 minutes, 2 minutes, 1 minute, or 30 seconds.

Figure 13:
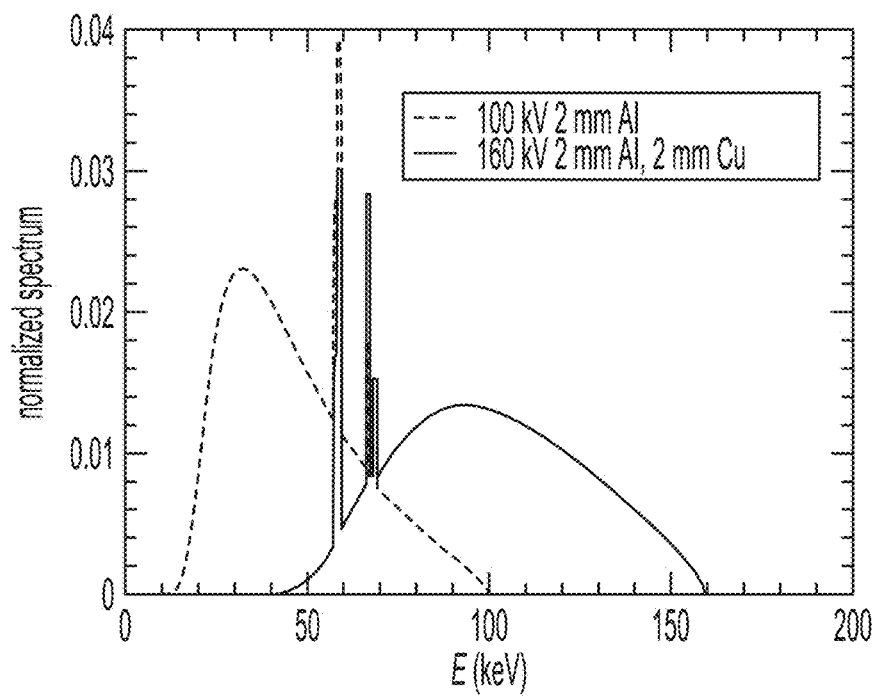
FIG. 13 is a graph showing calculated beam spectra at "high" energy and "low" energy.

Data was acquired for two different spectra, chosen to be similar to spectra used for dual-energy measurements in current checkpoint screening. Calculated spectra are shown in FIG. 13. The high energy spectrum, in blue, had an endpoint energy of 160 kV (but was reduced to 150 kV with the Hamamatsu source), 2 mm of copper and 2 mm of aluminum filtration. The average correlation length for this system, with the 285 LPI grid, was 90 nm. The low energy spectrum, shown in red, had an endpoint energy of 100 kV, 2 mm aluminum filtration, and an average correlation length of 170 nm.

Figure 14:
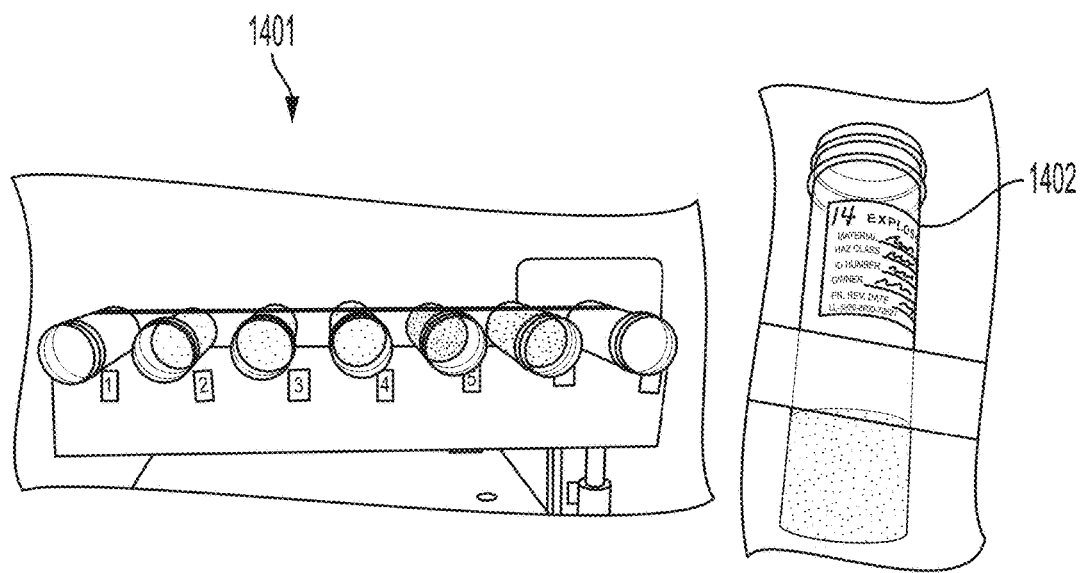
FIG. 14 shows a set of vials containing samples set for end-on imaging and a single vial containing explosive material.

The test dataset consisted of over 20 different benign materials, selected with knowledge of items typically found in baggage, and with a wide range of densities, effective atomic numbers, and including several items which were powdery or had other density variations. Four threat materials were selected, all with some level of mesoscale texture. Three of the materials were powders, with a range of grain sizes and preparation methods, and one was a moldable. Materials were placed in plastic cylinders 3 cm in diameter and 2-3 cm thick, had a total mass of 15-30 g per sample, and were imaged end-on to produce a large area with uniform thickness. An example vial 1402 and set of samples 1401 assembled for imaging are shown in FIG. 14.

Once data were acquired, the absorption/refraction/scatter images were extracted and the scatter image corrected for

TABLE 1

| Material | $\mu_H$ (cm$^{-1}$) | $\mu_L$ (cm$^{-1}$) | $\mu_L/\mu_H$ | $v_H$ (cm$^{-1}$) | $v_L$ (cm$^{-1}$) |
|---|---|---|---|---|---|
| raspberry jelly | 0.208 ± 0.008 | 0.285 ± 0.010 | 1.37 | −2.00E−03 ± 1.38E−02 | −2.25E−03 ± 2.49E−03 |
| strawberry jelly | 0.211 ± 0.006 | 0.287 ± 0.007 | 1.36 | −4.44E−05 ± 1.33E−02 | −9.30E−04 ± 2.45E−03 |
| coconut oil | 0.170 ± 0.004 | 0.285 ± 0.005 | 4.67 | 9.20E−05 ± 1.19E−02 | −1.32E−03 ± 2.64E−03 |
| rubber cement | 0.119 ± 0.001 | 0.150 ± 0.001 | 1.27 | −1.86E−04 ± 1.13E−02 | 2.83E−04 ± 2.02E−03 |
| Vaseline | 0.130 ± 0.008 | 0.177 ± 0.013 | 1.36 | 5.21E−04 ± 5.81E−03 | 2.97E−04 ± 2.53E−03 |
| Colgate | 0.191 ± 0.005 | 0.320 ± 0.008 | 1.67 | 3.63E−03 ± 6.45E−03 | 1.46E−02 ± 3.08E−03 |
| Olay sunscreen | 0.165 ± 0.006 | 0.308 ± 0.010 | 1.87 | 9.21E−03 ± 6.44E−03 | 3.33E−02 ± 3.16E−03 |
| pure honey | 0.194 ± 0.003 | 0.297 ± 0.004 | 1.54 | −5.31E−04 ± 6.88E−03 | −9.83E−04 ± 2.60E−03 |
| apricot scrub | 0.150 ± 0.005 | 0.237 ± 0.008 | 1.58 | 2.69E−04 ± 7.31E−03 | 4.84E−03 ± 3.37E−03 |
| kids sunscreen | 0.211 ± 0.005 | 0.520 ± 0.011 | 2.47 | 5.66E−02 ± 1.01E−02 | 1.70E−01 ± 9.20E−03 |
| Old Spice antiperspirant | 0.195 ± 0.004 | 0.425 ± 0.008 | 2.18 | 5.10E−03 ± 7.32E−03 | 1.62E−02 ± 4.40E−03 |
| Mitchum deodorant | 0.187 ± 0.005 | 0.339 ± 0.008 | 1.82 | 2.47E−03 ± 6.72E−03 | 7.62E−03 ± 2.98E−03 |
| Banana sunscreen | 0.151 ± 0.005 | 0.229 ± 0.008 | 1.52 | −1.60E−03 ± 6.28E−03 | −7.49E−03 ± 2.30E−03 |
| Banana kids sunscreen | 0.185 ± 0.005 | 0.399 ± 0.006 | 2.15 | 1.95E−02 ± 6.82E−03 | 6.47E−02 ± 4.34E−03 |
| AW toothpaste | 0.220 ± 0.006 | 0.366 ± 0.008 | 1.67 | 4.27E−03 ± 7.17E−03 | 3.12E−02 ± 4.77E−03 |
| sunflower oil | 0.133 ± 0.003 | 0.185 ± 0.003 | 1.39 | 2.44E−04 ± 5.76E−03 | 5.11E−04 ± 3.06E−03 |
| Nutella | 0.139 ± 0.013 | 0.269 ± 0.025 | 1.94 | 3.55E−03 ± 5.90E−03 | 4.01E−02 ± 4.92E−03 |
| water | 0.139 ± 0.002 | 0.213 ± 0.004 | 1.53 | 6.36E−05 ± 5.77E−03 | −1.08E−03 ± 2.08E−03 |
| flour | 0.121 ± 0.001 | 0.176 ± 0.002 | 1.46 | 6.74E−03 ± 6.55E−03 | 7.03E−02 ± 7.07E−03 |
| powdered sugar | 0.093 ± 0.003 | 0.135 ± 0.004 | 1.45 | 1.44E−02 ± 5.84E−03 | 1.28E−01 ± 5.23E−03 |
| Material A_6 | 0.184 ± 0.018 | 0.289 ± 0.005 | 1.57 | 2.59E−03 ± 6.57E−03 | 3.05E−02 ± 4.01E−03 |
| Material A_7 | 0.186 ± 0.003 | 0.280 ± 0.004 | 1.51 | 4.02E−03 ± 5.64E−03 | 2.92E−02 ± 3.79E−03 |
| Material A_5 | 0.193 ± 0.003 | 0.293 ± 0.005 | 1.52 | 3.84E−03 ± 6.18E−03 | 3.14E−02 ± 3.98E−03 |
| Material B_9 | 0.131 ± 0.010 | 0.191 ± 0.007 | 1.46 | 1.05E−03 ± 7.08E−03 | 2.44E−02 ± 7.07E−03 |
| Material B_121-1A | 0.135 ± 0.004 | 0.196 ± 0.006 | 1.45 | −5.38E−04 ± 6.02E−03 | 2.94E−02 ± 7.36E−03 |
| Material C_11 | 0.113 ± 0.002 | 0.169 ± 0.003 | 1.50 | 1.73E−02 ± 6.54E−03 | 1.15E−01 ± 7.03E−03 |
| Material C_14 | 0.067 ± 0.002 | 0.098 ± 0.004 | 1.46 | 1.62E−02 ± 4.80E−03 | 1.19E−01 ± 4.94E−03 |
| Material C_13 | 0.066 ± 0.002 | 0.096 ± 0.005 | 1.45 | 1.30E−02 ± 5.03E−03 | 1.16E−01 ± 5.52E−03 |
| Material C_10 | 0.110 ± 0.002 | 0.165 ± 0.005 | 1.50 | 1.36E−02 ± 8.81E−03 | 1.15E−01 ± 7.96E−03 |
| Material C_12 | 0.113 ± 0.002 | 0.167 ± 0.005 | 1.49 | 1.49E−02 ± 5.80E−03 | 1.14E−01 ± 7.25E−03 |
| Material C_18 | 0.105 ± 0.001 | 0.155 ± 0.003 | 1.48 | 3.19E−03 ± 8.05E−03 | 3.92E−02 ± 1.17E−02 |
| Material C_19A | 0.119 ± 0.001 | 0.177 ± 0.001 | 1.49 | 1.77E−02 ± 1.03E−02 | 1.52E−01 ± 8.06E−03 |
| Material C_7A | 0.151 ± 0.011 | 0.219 ± 0.021 | 1.45 | 9.33E−04 ± 7.80E−03 | 3.66E−03 ± 7.30E−03 |
| Material D_2 | 0.127 ± 0.018 | 0.178 ± 0.004 | 1.41 | 1.35E−03 ± 6.99E−03 | 1.91E−02 ± 9.51E−03 |
| Material D_1 | 0.120 ± 0.002 | 0.179 ± 0.004 | 1.49 | 1.89E−03 ± 6.70E−03 | 2.05E−02 ± 1.04E−02 |
| Material D_4 | 0.120 ± 0.003 | 0.180 ± 0.005 | 1.51 | 1.95E−03 ± 6.53E−03 | 1.59E−02 ± 9.95E−03 |
| Material D_3 | 0.121 ± 0.003 | 0.182 ± 0.005 | 1.51 | 1.39E−03 ± 6.70E−03 | 1.90E−02 ± 1.00E−02 | beam hardening. A region of interest was chosen, typically including most of the material, and mean and standard deviation values were extracted for both attenuation ($I/I_0$) and scatter ($V/V_0$). The attenuation was converted into an attenuation coefficient $\mu=-\ln(I/I_0)/t$, where t represents measured sample thickness, and $\mu$ is in units of mean free attenuation paths per cm ($cm^{-1}$). In analogous fashion, we extracted a scatter coefficient $v=-\ln(V/V_0)/t$, in units of mean free scatter paths per cm ($cm^{-1}$). Both quantities are implicitly weighted averages over all energies present in the spectrum. The variations observed in both absorption and scatter images were propagated as errors to obtain variation estimates for both quantities. This was performed for both the high and low energy spectra, and the quantitative results are shown in Table I: attenuation coefficient $\mu$ at low and high energy, and scatter coefficient $v$ at low and high energy, for each sample measured.

Figure 15:
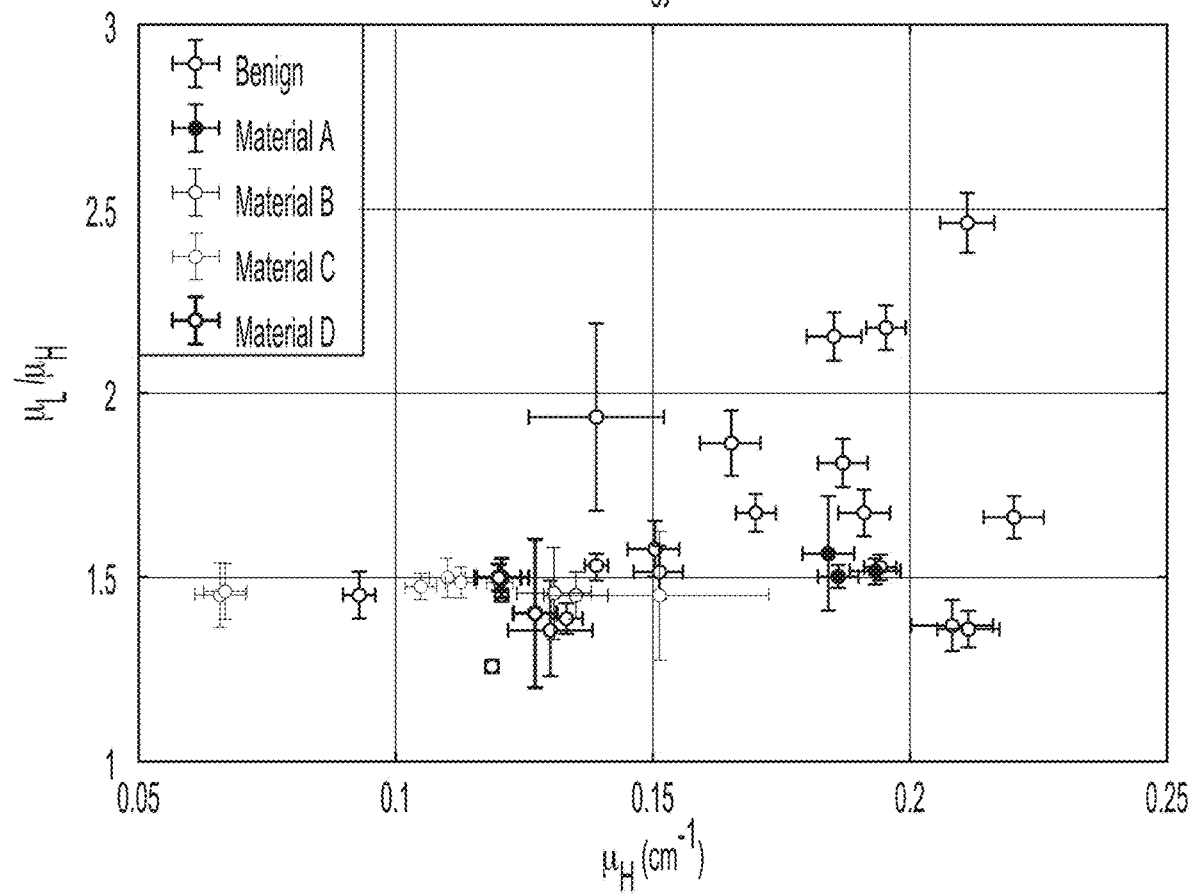
FIG. 15 is a graph showing Dual Energy Results. The y-axis indicates $\mu_L/\mu_H$, which can be related to $Z_{eff}$, and the x-axis is $\mu_H$, which can be related to density. Materials A-D represent four different explosive materials and encompass a number of preparations.

The attenuation coefficients extracted from the phase contrast measurements can be interpreted in the same manner as conventional dual energy measurements, which are analyzed to estimate effective atomic number $Z_{eff}$ and density $\rho$. Here, we examined the ratio of the low energy and high energy attenuation coefficients ($\mu_L/\mu_H$); for a fully calibrated system this quantity can be related to the effective atomic number $Z_{eff}$. In FIG. 15 we plot $\mu_L/\mu_H$ as a function of $\mu_H$, which can be mapped approximately to density. Error bars indicate the variation observed within each sample.

Benign materials were shown in black. Water was indicated at $\mu_H$=0.139 and $\mu_L/\mu_H$=1.53; a number of other benign materials had $Z_{eff}$ similar to water, but at higher densities many of the benign materials also exhibited higher $Z_{eff}$. Threat materials were labeled by letters; with each letter signifying a single material, but samples within each group may have different preparation conditions. Material A showed a $Z_{eff}$ similar to water but the density is significantly larger. Materials B and D were close to water in density and $Z_{eff}$, although slightly lower in both. Material C exhibited a wide range of densities corresponding to different preparation conditions, but $Z_{eff}$ still close to that of water. In all four material categories, at least some of the samples exhibited density/$Z_{eff}$ which were consistent with benign materials.

Figure 16:
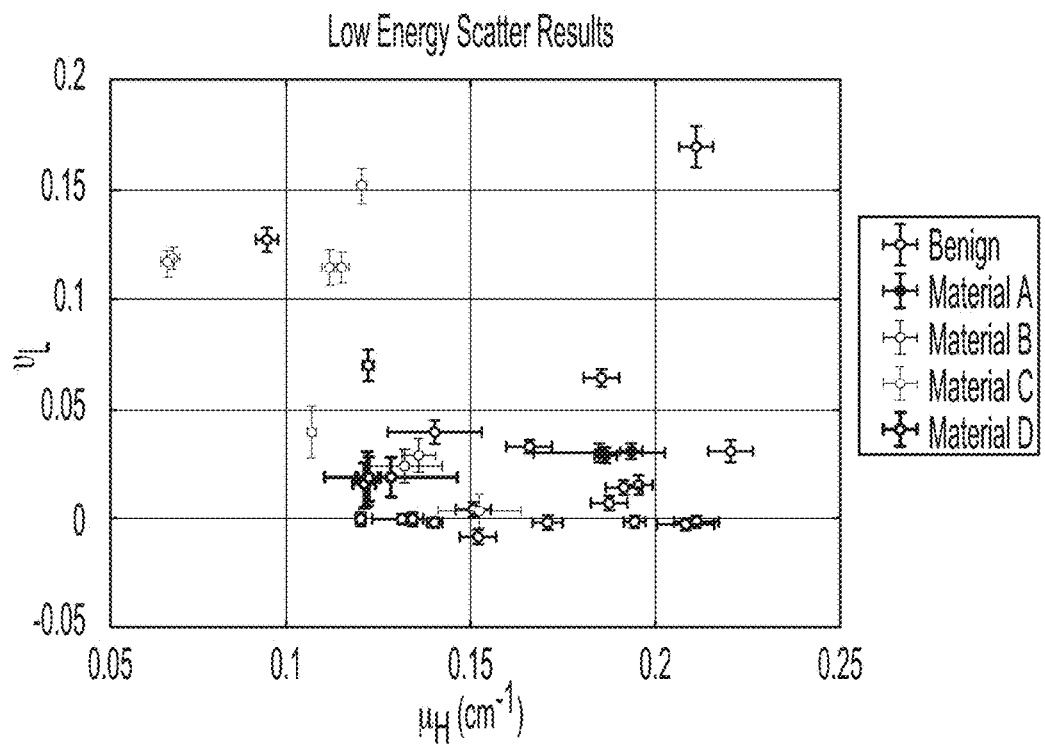
FIG. 16 is a graph showing scatter coefficient at low energy $v_L$ as a function of $\mu_H$ (proportional to density). Explosives are labeled by letters A-D.

Next, we examined material properties revealed by scatter, plotting the scatter coefficient for the lower energy spectrum, $v_L$, as a function of density (approximated as $\mu_H$), shown in FIG. 16. Note that a scatter coefficient of zero indicates no scatter was detected from a given material. The first qualitative observation we can make is that this plot is distinct from the dual energy information, with the distribution of properties clearly different than the previous plot, indicating that unique information is being displayed. For Materials A, B, and D, a small but significant amount of scattering is present. Note that in most cases, this distinguishes them from materials with otherwise similar density and atomic number. Material C covers not only a wide range of densities, but also a wide range of textures, from apparently homogeneous to very highly scattering, depending on the preparation method used.

The range of scatter values in the benign materials can be helpful for discrimination as well. At low density, powdered sugar ($\mu_H$=0.093, $v_L$=0.13) exhibits very high scattering; flour is also fairly highly scattering ($\mu_H$=0.12, $v_L$=0.07). Nutella® exhibits a moderate amount of scattering ($\mu_H$=0.14, $v_L$=0.04). There were four different types of sunscreen, which illustrate an interesting range of scattering properties. One of the sunscreens, Banana Boat® ($\mu_H$=0.15, $v_L$=−0.007), is an organic sunscreen and contains no metals; it is relatively low in density and no significant scatter is observed. Olay® sunscreen ($\mu_H$=0.17, $v_L$=0.033) contains 3% ZnO particles and exhibits some scatter. Banana Boat Kids® contains 6% $TiO_2$ and 4% ZnO and shows higher scatter yet ($\mu_H$=0.19, $v_L$=0.065). The final sunscreen (Badger® brand kids sunscreen) shows high $Z_{eff}$, high density, and high scatter ($\mu_H$=0.21, $v_L$=0.17); it includes 19% ZnO particles, nearly as high of a concentration as our scatter step wedges. Other materials which show a small amount of scatter include deodorants and toothpaste, as can be seen in Table I. Note that materials which are homogeneous, such as water, sunflower oil, honey, and Vaseline®, display scatter values consistent with zero, confirming that the beam hardening correction process is successfully accounting for fringe visibility changes associated with spectral changes.

Figure 17:
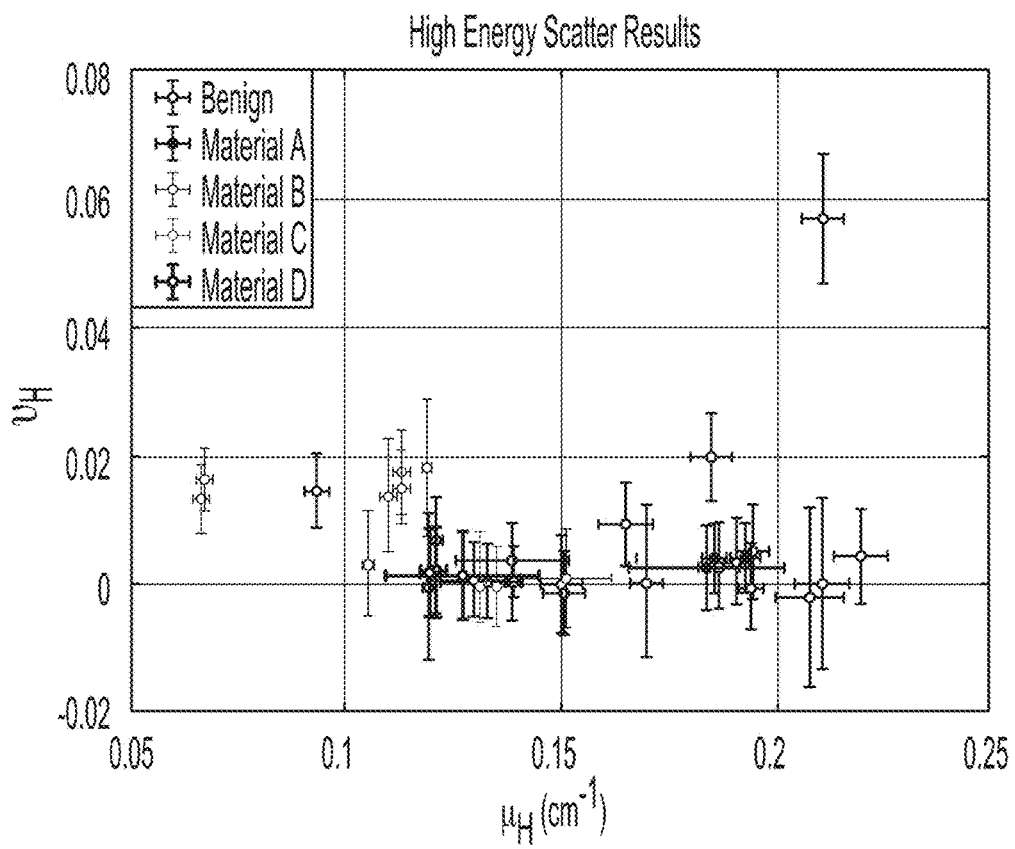
FIG. 17 is a graph showing scatter coefficient at high energy $v_H$ as a function of $\mu_H$ (proportional to density). Explosives are labeled by letters A-D.

For the higher energy spectrum, the absolute values of all the scatter coefficients are reduced, as shown in FIG. 17. Several of the more weakly scattering samples cannot be distinguished from non-scattering materials, but the more strongly scattering materials are still distinguishable. Detailed numerical results can be seen in Table I.

Often, not all pixels on the detector will record x-rays. Scratches or other damage can leave patterns of dead pixels. If not corrected, or if corrected using linear interpolation which is typically used for x-ray imaging, this can introduce artifacts into the reconstructed scatter and phase contrast images. The grating is typically aligned with the detector array, producing a pattern of vertical stripes. The grating period is typically chosen so that its period on the image is a few pixels. The image may show vertical intensity oscillations with a longer period, which might be a Moire pattern between the grating shadows and the pixel boundaries. The value of any given pixel (x, y) of the grating image will be designated g(x, y), and the image size will be $N_x \times N_y$ pixels. FIG. 18A includes an image of a region of the grating image, showing the vertical grating lines and the longer period Moire pattern. Near the center is a line of bad pixels from a scratch on the detector. FIG. 18B is a grating image with both the object and detector gratings in a section of bad pixels.

FIGS. 19A-19C include Fourier transforms of grating images. In FIG. 19A, a section of the Fourier transform of the grating image shows the central peak at (0, 0) and the first order harmonic peaks on either side at (±613, ±9). The non-zero y values of the first harmonic peak indicate that the grating was not perfectly aligned with the detector in this image. In FIG. 19B, a close-up of a region of the center of the Fourier Transform of the grating image shows the central peak at (0, 0) and Moire peaks at (±10, 0). In FIG. 19C, a close-up of the region around the first harmonic shows the harmonic peak at (613, −9) and convolutional Moire peaks at (603, −9) and (623, −9).

The Fourier transform of the grating image shows peaks at the origin and near the x-axis representing the Moire period, the grating period, and at intervals of the Moire period on either side of the grating period. If the grating period is long enough, higher harmonics of the grating will show up although typically the grating spacing and placement are chosen so that only the first harmonic appears. If a detector grid is present, peaks will be present at the detector grid period and its harmonics, as well as cross-harmonics between the detector and object grid. The grating Fourier transform will be denoted G(x, y).

After subtracting the dark image, bad pixels typically have values near zero. The grating image, despite its features, is usually relatively low contrast. A simple threshold cut-off on the grating image is usually effective for selecting pixels to fix.

The bad pixel detection can be made even better by reducing major sources of large period variation within the grating image. A copy G'(x, y) is made of the Fourier transform of the grating image, and the regions around the central peak and the grating harmonic peak pairs are removed, making sure to include the Moire satellites around the major peaks. Let $p_M$ be the Moire period in the grating image, $(p_{ox}, p_{oy})$ be the location of the first harmonic peak of the object grid, and $(p_{dx}, p_{dy})$ be the first harmonic peak of the detector grid. An acceptable filter is to choose $r_1=2p_M$ and $r_2=10p_M$, and then use:

$$r(x, y) = \sqrt{x^2 + y^2} \quad (1)$$

$$F(x, y) = \begin{cases} 1 & r(x, y) > r_2 \\ 0 & r(x, y) < r_1 \\ \frac{1}{2}[1 - \cos(\pi(r(x,y) - r_1)/(r_2 - r_1))] & \text{otherwise} \end{cases} \quad (2)$$

$$G'(x, y) = G(x, y) \prod_{j=-n_o}^{n_o} \prod_{k=-n_d}^{n_d} F(x + jp_{ox} + kp_{dx}, y + jp_{oy} + kp_{dy}). \quad (3)$$

where $n_o$ is the number of harmonic peaks of the object grid and $n_d$ is the number of harmonic peaks of the detector grid.

This is then Fourier transformed back to give the image $g_0$ (x, y). The bad pixels, being isolated aperiodic features, are composed primarily of high frequency components so the inverse Fourier transform preserves these structures. Since the zero-period component has been removed, the average value of the image will be zero. With most structure removed, almost all pixels will have values near zero while the dead pixels will have highly negative values. All pixels with values lower than a threshold value will be considered bad and removed. A reasonable threshold is −G(0, 0)/3.

Because Fourier analysis based on convolutional patterns around the harmonic peaks are used for producing the scatter and phase contrast images, simply replacing a bad pixel by the average of its neighbors is insufficient. This neglects the short scale variation on the order of the grid pattern that is crucial to the analysis. Instead, we will use the idea that in the vicinity of any pixel out to a radius of a few pixels, the pixel values can be approximated by contributions from all harmonic and cross-harmonic peaks from the gratings. FIG. 20 includes a Fourier transform of a grating image with both an object and detector grid, showing first and second harmonics as well as cross-harmonics.

$$g(x, y) \approx \sum_{j=-n_o}^{n_o} \sum_{k=-n_d}^{n_d} b_{(jk)} e^{2\pi i \left((jp_{ox}+kp_{dx})x/N_x + (jp_{oy}+kp_{dy})y/N_y\right)}. \quad (4)$$

The $b_{(jk)}$ are complex fitting parameters. Because g(x, y) is real, $b_{(00)}$ must be real and $b_{(-j-k)} = b^*_{(jk)}$. However, there is no need to include these constraints in the algorithm, since unconstrained linear least squares fitting via singular value decomposition (SVD) is robust, simple, and reliable. Since this fit extends to several pixels around the bad pixel, detailed features within this region can be washed out for the fit. However, the image analysis technique involves a low-pass filter so that these details will be lost anyway. Despite the matrix-like terminology, conceptually in the fitting process b is a vector and the pair (jk) is treated as a single index. This can be accomplished with a mapping of (jk) to an index I running from 0 to I max=$(1+2n_o)(1+2n_d)$.

Choose a starting fitting step $r_f$ as the number of pixels in x and y to either side of the bad pixel to include in the fit. This should be chosen so that $1+2r_f$ at least covers one grating period. In addition, if entire columns of bad pixels are expected, it should be at least 2 to avoid ill-conditioned fits. For any given bad pixel at $(x_b, y_b)$, scan over all pixels (x, y) such that $x_b-r_f \le x \le x_b+r_f$ and $y_b-r_f \le y \le y_b+r_f$. If the $n^{th}$ scanned pixel (starting from n=0) is not bad, add its value $g(x_n, y_n)$ to the vector h of nearby good pixel values $$h_x = g(x_n, y_n) \quad (5)$$

and add a row to the matrix of fitting vectors A $$A_{i,I} = e^{2\pi i((jp_{ox}+kp_{dx})x_n/N_x + (jp_{oy}+kp_{dy})y_n/N_y)}. \quad (6)$$

Let h have m elements, so that A is m×I max in size. If m<$I_{max}$, the fit will be ill-conditioned—there will be more fit variables $b_j$ than constraints $h_i$. Even m=I max is likely to lead to poor results. A reasonable criterion is to have the problem over-determined by a factor of 2. If m<6, increase $r_f$ by 1 and find h and A again; repeat until m≥2 $I_{max}$.

The problem is now a complex linear fit, h=A·b. This is solved by finding the SVD of A.

$$A = U \cdot W \cdot V$$

where V is a $I_{max} \times I_{max}$ unitary matrix, W is a $I_{max} \times I_{max}$ non-negative real diagonal matrix, and U is a m×$I_{max}$ matrix which is column orthonormal $$u_j \cdot u_k = \delta_{jk},$$

$u_j$ is the $j^{th}$ column of U, and the symbol · indicates the inner product. The elements on the diagonal of W are called the singular values. The condition number of A is the ratio of the largest to the smallest of the singular values. If the condition number of W is more than 10, increase $r_f$ by 1 and find h and A again.

Let $W^{-1}$ be the pseudo-inverse of W; a $I_{max} \times I_{max}$ diagonal matrix such that $$\tilde{W}_{ii}^{-1} = \begin{cases} 0 & \text{if } W_{ii} = 0 \\ 1/W_{ii} & \text{otherwise} \end{cases}.$$

The fit vector is then found by $$b = V \cdot \tilde{W}^{-1} \cdot U^\dagger \cdot h.$$

(It is worth noting that since we demand the condition number is finite, all $W_{ii}$ will be non-zero so that $W^{-1} = \tilde{W}^{-1}$.) Finally, set $$g(x_b, y_b) = \sum_{l=0}^{l_{max}} b_l e^{2\pi i((jp_{ox}+kp_{dx})x_b/N_x + (jp_{oy}+kp_{dy})y_b/N_y)}$$

Then repeat the procedure where h is filled with pixel values from the grating+object image, replacing the bad pixel in the grating+object image with the fitted value (A does not change between the grating and grating+object image, so it can be re-used and its SVD does not have to be re-computed).

If the grating absorption modulation is low compared to the average value of the image, the cross-harmonic peaks can be neglected. For images with a detector grid, a fairly long grating period (resulting in multiple harmonic peaks) in one or both grids, and many bad pixels, this can potentially result in significant time savings due to the O(m$I_{max}^2$) scaling of SVD.

Figures 24A, 24B:
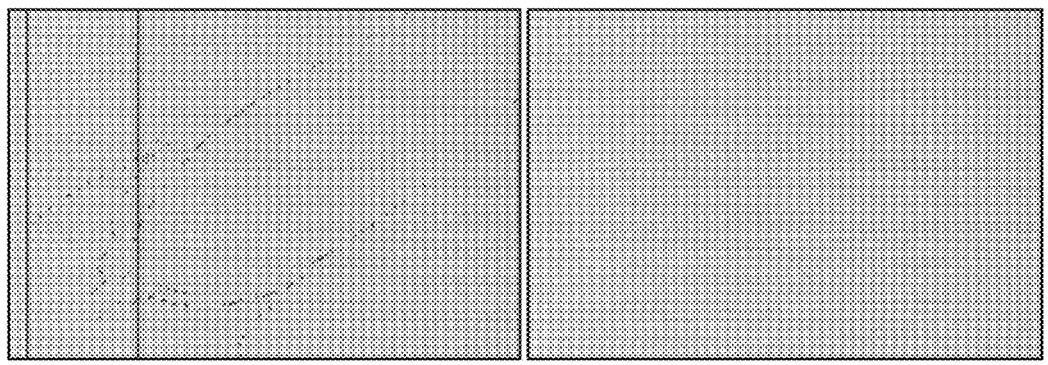
FIGS. 24A and 24B are images of a region of bad pixels with both a detector and an object grid, and with contributions from the second harmonic peaks of both grids before and after bad pixel correction, respectively.
Figure 25:
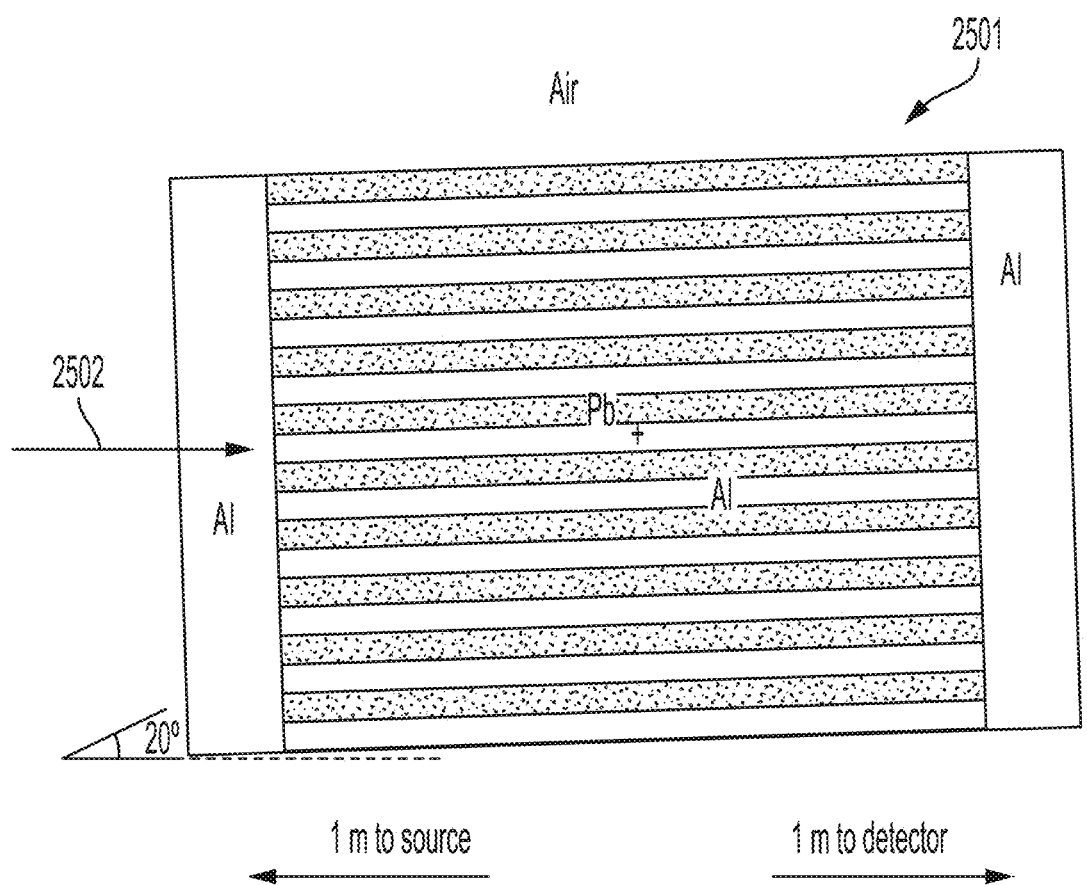
FIG. 25 is a schematic illustrating grid (i.e., grating) tilt. The beam direction is indicated by the arrow 2502.

FIGS. 21 and 22 give examples of the bad pixel detection (FIGS. 21A and 22A) and correction algorithm (FIGS. 21B and 22B). FIGS. 23 and 24 show how fixing bad pixels improves the reconstructed phase and scatter images (FIGS. 23A and 24A are before correction, FIGS. 23B and 24B are after correction), respectively. FIG. 25 is an example of bad pixel correction with both an object and detector grating and with contributions from multiple harmonics from both gratings (FIG. 25B is after bad pixel correction).

In some embodiments, the signal-to-noise ratio in the acquired data can be significantly improved by tilting the source grating, the object grating, the detector grating, or combinations thereof. Tilting can effectively make line sources narrower without the burden of physically manufacturing gratings with extremely narrow grating elements (i.e. parallel channels with high aspect ratios). Tilting can comprise rotating the gratings about an axis parallel to grating element lines. In certain embodiments wherein the grating elements are parallel channels (each channel having a width and a height), the amount of tilt is greater than zero degrees and less than or equal to a maximum angle equivalent to the arctangent of the width of the channel divided by the height.

Referring to FIG. 25, a schematic illustration depicts a grating 2501 having 210 parallel lines per inch and utilizing a 2 degree tilt relative to an incident beam 2502 from an x-ray source. Experimentally observed visibility changes with grid tilt were simulated and the simulation results are discussed herein. The geometry and materials of the measurement conditions were set up in a transport model to calculate the total flux at the detector for various grid tilt (i.e., rotation) angles. The flux in an array of 48 μm pixels is tallied with MCNP 6.1—a Monte Carlo transport code to determine the pixel-based amplitude to average flux ratio. While the physics of the SAXS signal induced by a test object is not included in the purely atomic number-atomic mass (ZAID) based cross section libraries, the no-object visibility (to undergo reduction from object scatter) can be computed. Ideally this quantity should be as large as is obtainable for the greatest sensitivity.

Figure 26A:
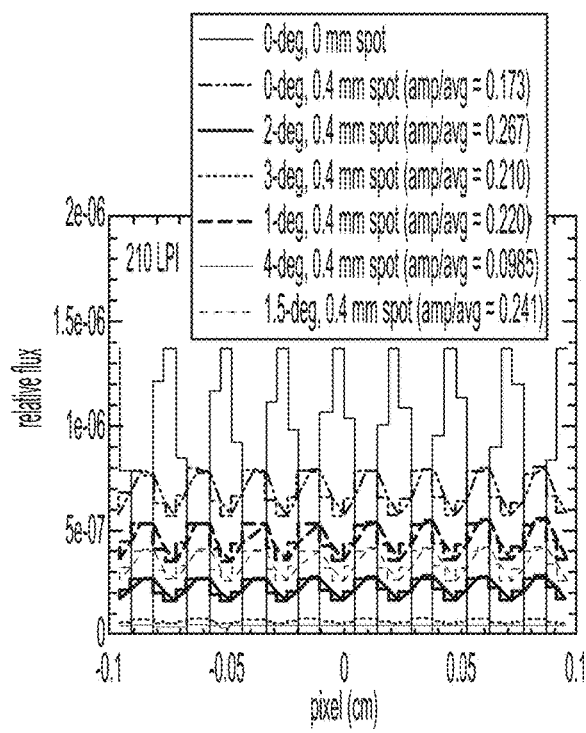
FIGS. 26A and 26B are graphs showing modeled flux at the detector from a 0.4 mm spot size 100 kVp source showing values of fringe visibility fits (26A), and plot of fringe visibility ($H_1/H_0$) along with the second harmonic ratio ($H_2/H_0$) as a function of rotation angle (26B).
Figure 26B:
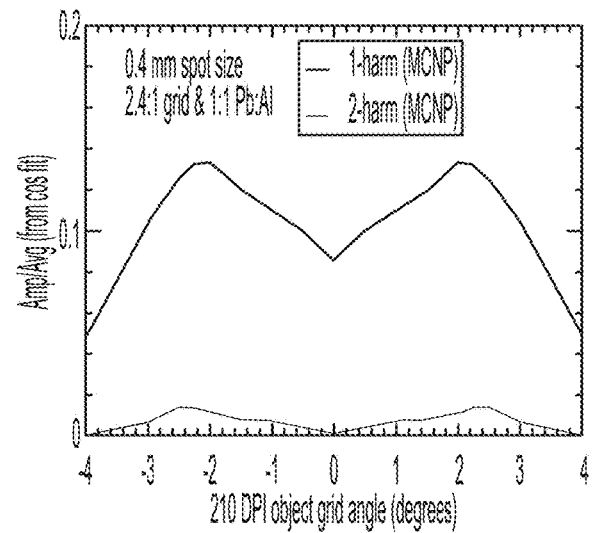

FIGS. 26A and 26B show modeled flux at the detector from a 0.4 mm spot size 100 kVp source showing values of fringe visibility fits (26A), and plot of fringe visibility ($H_1/H_0$) along with the second harmonic ratio ($H_2/H_0$) as a function of rotation angle (27B). FIG. 26A shows the modeled flux at the detector for various rotation angles. The grid visibility for each angle is determined from a fit to the first two harmonics and is plotted in FIG. 26B. As is in the measurement, a local minimum in visibility appears at zero degrees and increases symmetrically for angular changes from zero with a maximum value just before the fully transmitted grid openings go to zero.

Figure 27A:
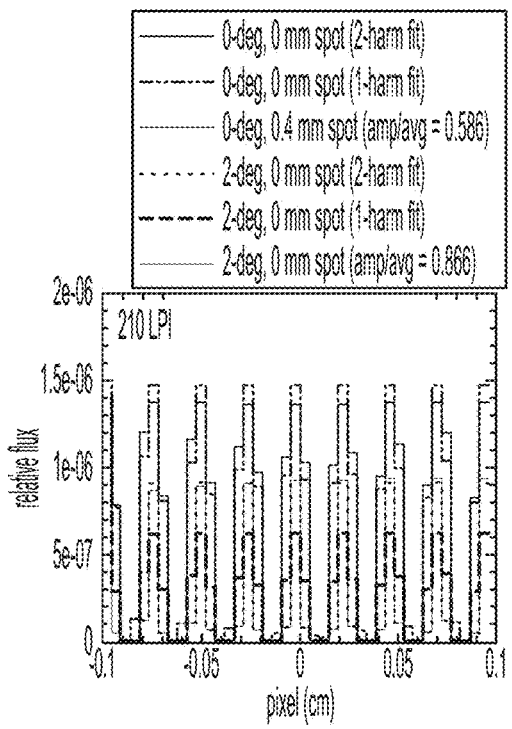
FIGS. 27A and 27B are graphs showing modeled flux at the detector from a 0 mm spot size 100 kVp source showing values of fringe visibility fits (27A), and plot of analytical fringe visibility ($H_1/H_0$) for perfect (Pb) attenuation and a parallel beam source (27B).
Figure 27B:
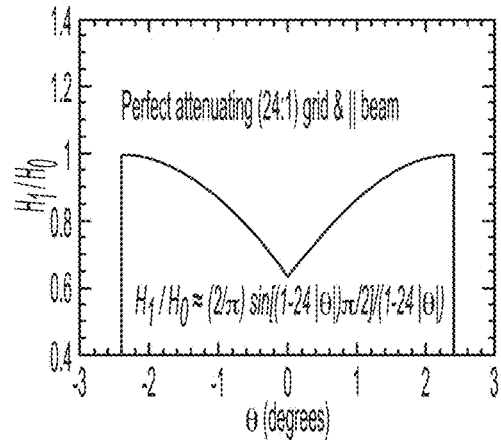

This behavior for x-rays emitted from a 0.4 mm spot at 2 m from the detector is very unexpected. A hint at its underlying origin is revealed by considering an idealized signal from a 0 mm spot (FIG. 27A) or even more strikingly from an idealized parallel beam (FIG. 27B). FIG. 28B shows that an obvious consequence of grid rotation is an effective reduction of transmitted duty-cycle. While a reduction of the fringe amplitude or first harmonic can be seen for increasing $|\theta|$ (smaller effective duty-cycle), the fringe average is reduced by an even greater amount resulting in increased ratio visibility and thus increased scatter sensitivity. Additionally, in the limit of parallel beam and perfect attenuation of the lead, an analytical relationship for harmonic ratios is simply $$\left(\frac{H_n}{H_0}\right)_{\parallel} = \frac{P}{\pi n s}\sin\frac{\pi n s}{P}$$

where s is the effective slit width for the rotated grid. Assuming perfect attenuation for the lead absorber regions the effective slit width as a function of rotation angle is given by $$\frac{s}{P} = \frac{1}{2} - \frac{T}{2s_{1:1}}|\theta|,$$

where P is the grid period, T is the grid thickness, s 1:1 is the width of the transmitting slits for the 1:1 duty-cycle grid and θ is the "small" rotation angle. Also, the effective duty-cycle ($d_c$:1) can then be expressed with $$d_c = \frac{s}{P-s}.$$

In the parallel beam case it is interesting to note that the first harmonic ratio is a maximum when both s/P and the intensity go to zero.

Figure 28:
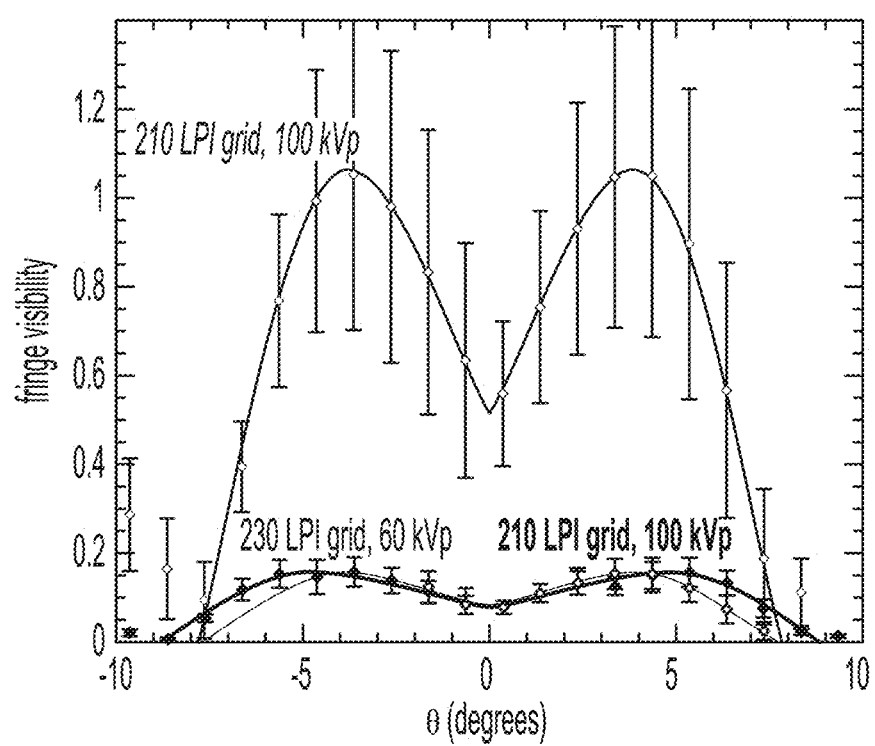
FIG. 28 is a graph showing the modeled fits to fringe visibility measurements with a tilted object grating.

This behavior is relaxed by the more appropriate non-parallel beam and finite spot size physics. The s/P equation above still assumes perfect attenuation, but not a parallel beam and can be used as an approximate mapping from simulated rotation to simulated duty-cycle. A consequence of this mapping is that the analytical relationship for harmonic ratios above can be empirically modified to give a reasonably accurate fit to the non-parallel beam data with $$\frac{H_1}{H_0} = a_0 \frac{\sin[a_3(1-a_1|\theta|+a_2\theta^2)]}{1-a_1|\theta|+a_2\theta^2}$$

where $a_j$ are four fit parameters. Interpreting $a_1$ as $T/s_{1:1}$ and given θ for the maximum $H_1/H_0$, the equations for s/P and for $d_c$ can be used to infer the grid duty-cycle having maximum sensitivity. FIG. 28 shows that the modified harmonic ratio gives very reasonable fits to rotated object grid measurements indicating that the effect is due to a change in duty-cycle even when the source deviates from a parallel beam. Using the modified harmonic ratio fits, the maximum fringe visibility gives an approximate effective duty-cycle 1:7 for both the 210 LPI grids and 1:4 for the 230 LPI grid.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A method comprising:
   emitting source x-rays from a polychromatic source operating at an endpoint energy greater than or equal to 100 keV and generating a spot size greater than or equal to 0.5 mm;
   creating a series of periodically repeating apparent sources from the source x-rays using a source grating;

patterning the series of periodically repeating apparent sources into a patterned beam using an object grating placed proximal to an object to be imaged and at distances $L_1$ from the source grating and $L_2$ from a detector grating, wherein the source, object, and detector gratings have respective grating elements, wherein the periodicities, P, of the source and object grating elements are related by $P_{source}=P_{object}*[(L_1+L_2)/L_2]$ and wherein the source and object grating elements are substantially parallel;

acquiring through the detector grating a first image with the object and a second image without the object, wherein the detector grating elements are oriented substantially orthogonally relative to the object grating elements and a beam axis and wherein the object grating and the detector grating have a substantially equivalent x-ray attenuating factor;

measuring visibilities of the object grating from the first and second images to determine an object grating visibility reduction due to scatter and beam hardening;

measuring visibilities of the detector grating from the first and second images to determine a detector grating visibility reduction due to beam hardening; and applying a beam hardening correction based on a comparison of the object grating visibility reduction and the detector grating visibility reduction to generate a corrected scatter image.

2. The method of claim 1, further comprising operating the polychromatic source at an endpoint energy greater than or equal to 150 keV, 160 keV, 175 keV, 200 keV, or 450 keV.

3. The method of claim 1, further comprising tilting the object grating and detector grating by rotating the gratings about an axis parallel to grating element lines.

4. The method of claim 1, further comprising tilting the source grating by rotating the grating about an axis parallel to grating element lines.

5. The method of claim 1, wherein the acquiring includes detecting the images with a detector, wherein the object grating is approximately equidistant between the source and the detector.

6. The method of claim 5, wherein the detector grating has a periodicity, $P_{detector}$, equivalent to that of the source grating, $P_{source}$.

7. The method of claim 1, wherein the object and detector gratings comprise an equivalent material and have an equivalent thickness.

8. The method of claim 1, wherein the source grating, object grating, detector grating, or combinations thereof have grating elements comprising a parallel line pattern.

9. The method of claim 1, wherein the object to be imaged is a scatter test object calibration standard and further comprising performing a calibration of x-ray scatter, the scatter test object calibration standard comprising metal or metal oxide particles distributed in a polymer matrix and having a stepped-wedge geometry of at least three different thicknesses.

10. The method of claim 1, wherein the object to be imaged is a beam hardening test object calibration standard and further comprising performing a calibration of beam hardening, the beam hardening test object calibration standard comprising three or more homogeneous materials in a range of atomic numbers, with no large density variations on length scales between 10 nm and 200 microns, and have a thickness such that 10-90% of the x-ray intensity is transmitted through the test object.

11. A system comprising:

A polychromatic x-ray source configured to provide source x-rays at an endpoint energy greater than or equal to 100 keV and a spot size greater than 0.5 mm;

A detector;

A source grating configured to create a series of periodically repeating apparent sources from the source x-ray;

An object grating proximal to a position of an object to be imaged and at distances $L_1$ from the source grating and $L_2$ from a detector grating, wherein the periodicities of the source and object gratings are related by $P_{source}=P_{object}*[(L_1+L_2)/L_2]$, the object grating configured to pattern the series of periodically repeating apparent sources into a patterned beam;

The detector grating having detector grating elements that are oriented orthogonally relative to object grating elements and a beam axis, the detector and object gratings having an equivalent x-ray attenuation factor; and Processing circuitry operably connected to the detector and configured to execute computer-readable instructions to:
  Acquire through the detector grating a first image with the object and a second image without the object;
  Measure visibilities of the object grating from the first and second images to determine an object grating visibility reduction due to scatter and beam hardening;
  Measure visibilities of the detector grating from the first and second images to determine a detector grating visibility reduction due to beam hardening;
  apply a beam hardening correction based on a comparison of the object grating visibility reduction and the detector grating visibility reduction to generate a corrected scatter image.

12. The system of claim 11, wherein the polychromatic source is configured to provide source x-rays at an endpoint energy greater than or equal to 150 keV, 160 keV, 175 keV, 200 keV, or 450 keV.

13. The system of claim 11, wherein the object grating and detector grating are positioned such that the object grating elements and the detector grating elements are tilted by a rotation of the gratings about an axis parallel to grating element lines.

14. The system of claim 11, wherein the source grating is positioned such that source grating elements are tilted by a rotation of the grating about an axis parallel to grating element lines.

15. The system of claim 11, wherein the object grating is positioned approximately equidistant between the source and the detector.

16. The system of claim 15, wherein the detector grating has a periodicity, $P_{detector}$, equivalent to that of the source grating, $P_{source}$.

17. The system of claim 11, wherein the detector grating abuts the detector.

18. The system of claim 11, wherein the object and detector gratings comprise an equivalent material and have an equivalent thickness.

19. The system of claim 11, wherein the source grating, object grating, detector grating, or combinations thereof have grating elements comprising a parallel line pattern.

20. A non-transitory computer readable storage medium storing one or more programs, the one or more programs comprising instructions, which when executed by one or more processors operably connected to an x-ray imaging system that comprises:

A polychromatic x-ray source configured to provide source x-rays at an endpoint energy greater than or equal to 100 keV and a spot size greater than 0.5 mm;

A source grating configured to create a series of periodically repeating apparent sources from the source x-ray;

An object grating proximal to a position of an object to be imaged and at distances $L_1$ from the source grating and $L_2$ from a detector grating, wherein the periodicities of the source and object gratings are related by $P_{source}=P_{object}*[(L_1+L_2)/L_2]$, the object grating configured to pattern the series of periodically repeating apparent sources into a patterned beam; and The detector grating having detector grating elements that are oriented orthogonally relative to object grating elements and a beam axis, the detector and object gratings having an equivalent x-ray attenuation factor;

Cause the x-ray imaging system to:

Acquire through the detector grating a first image with the object and a second image without the object;

Measure visibilities of the object grating from the first and second images to determine an object grating visibility reduction due to scatter and beam hardening;

Measure visibilities of the detector grating from the first and second images to determine a detector grating visibility reduction due to beam hardening;

apply a beam hardening correction based on a comparison of the object grating visibility reduction and the detector grating visibility reduction to generate a corrected scatter image.

21. The non-transitory computer readable storage medium of claim 20 storing one or more programs, the one or more programs comprising instructions, which when executed by one or more processors operably connected to the x-ray imaging system cause the x-ray imaging system to perform a calibration, wherein the object to be imaged is a scatter test object, a beam hardening test object, or both.

\* \* \* \* \*